(12) United States Patent
Yoon et al.

(10) Patent No.: US 12,103,909 B2
(45) Date of Patent: Oct. 1, 2024

(54) POLYCYCLIC AROMATIC HYDROCARBON-BASED COMPOUNDS FOR MOLECULAR ELECTRONIC DEVICE AND MOLECULAR ELECTRONIC DEVICES COMPRISING SAME

(71) Applicant: Korea University Research and Business Foundation, Seoul (KR)

(72) Inventors: Hyo Jae Yoon, Seoul (KR); Soo Jin Cho, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 1011 days.

(21) Appl. No.: 17/052,270

(22) PCT Filed: Apr. 25, 2019

(86) PCT No.: PCT/KR2019/004996
§ 371 (c)(1),
(2) Date: Mar. 22, 2021

(87) PCT Pub. No.: WO2019/209039
PCT Pub. Date: Oct. 31, 2019

(65) Prior Publication Data
US 2021/0367154 A1 Nov. 25, 2021

(30) Foreign Application Priority Data

Apr. 26, 2018 (KR) .................. 10-2018-0048265

(51) Int. Cl.
*C07C 321/20* (2006.01)
*C07C 321/06* (2006.01)
(Continued)

(52) U.S. Cl.
CPC .......... *C07C 321/20* (2013.01); *C07C 321/06* (2013.01); *C07C 321/10* (2013.01);
(Continued)

(58) Field of Classification Search
None
See application file for complete search history.

(56) References Cited

U.S. PATENT DOCUMENTS

| 10,883,000 B1* | 1/2021 | Yang | ...................... C09D 5/086 |
| 2011/0108793 A1* | 5/2011 | Wessels | .............. H10K 19/202 |
| | | | 257/E21.04 |

FOREIGN PATENT DOCUMENTS

| JP | 2002-51774 A | 2/2002 |
| JP | 2008140883 A * | 6/2008 |

(Continued)

OTHER PUBLICATIONS

English machine translation PDF of JP 2008-140883A (Natsume et al.) accessed online from Espacenet. (Year: 2008).*

(Continued)

*Primary Examiner* — Katie L. Hammer
(74) *Attorney, Agent, or Firm* — NSIP Law

(57) ABSTRACT

The present invention relates to polycyclic aromatic hydrocarbon-based compounds, for a molecular electronic device, enabling molecular rectification, and molecular electronic devices comprising a molecular layer formed by means of the compounds self-assembled on an electrode. The compounds according to the present invention can realize rectifying properties by being introduced between electrodes and thus enable a high rectification ratio by means of low voltage driving, and thus can be substituted for a silicon-based diode device and, more particularly, can be utilized for a wearable device, Bluetooth, an IoT enabling device and the like which require low voltage driving.

6 Claims, 12 Drawing Sheets

(51) Int. Cl.
  *C07C 321/10* (2006.01)
  *H01B 1/06* (2006.01)
  *H01L 29/861* (2006.01)
  *H10K 10/00* (2023.01)
  *H10K 85/60* (2023.01)

(52) U.S. Cl.
  CPC ............ *H01B 1/06* (2013.01); *H10K 10/701* (2023.02); *H10K 85/622* (2023.02); *H10K 85/623* (2023.02); *C07C 2603/50* (2017.05); *H01L 29/861* (2013.01)

(56) References Cited

FOREIGN PATENT DOCUMENTS

| KR | 10-2004-0035206 A | 4/2004 |
|---|---|---|
| KR | 10-2006-0084735 A | 7/2006 |
| KR | 10-0825753 B1 | 4/2008 |
| KR | 10-2016-0057642 A | 5/2016 |

OTHER PUBLICATIONS

Xu, Qingmin, et al., "Controlled assembly of large π-conjugated aromatic thiols on Au (111)", *Nanotechnology*, vol. 19, Issue 13, 2008 (pp. 1-11).

Yoon, Hyo Jae, et al., "The Rate of Charge Tunneling through Self-Assembled Monolayers Is Insensitive to Many Functional Group Substitutions", *Angewandte Chemie*, vol. 124, Issue 19, 2012 (pp. 4736-4739).

Korean Notice of Allowance issued on Dec. 11, 2019 in counterpart Korean Patent Application No. 10-2018-0048265 (2 pages in Korean).

International Search Report issued on Aug. 23, 2019 in counterpart International Patent V Application No. PCT/KR2019/004996 (2 pages in English and 2 pages in Korean).

\* cited by examiner

[Fig. 1]
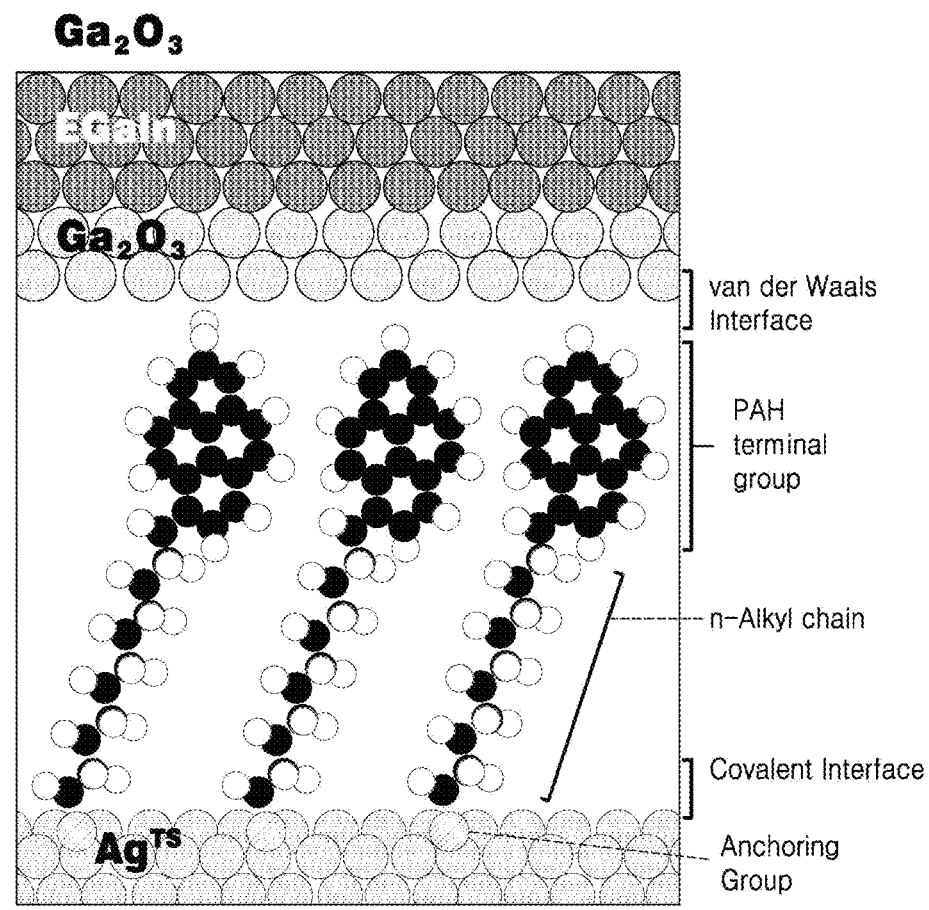
[Fig. 2]
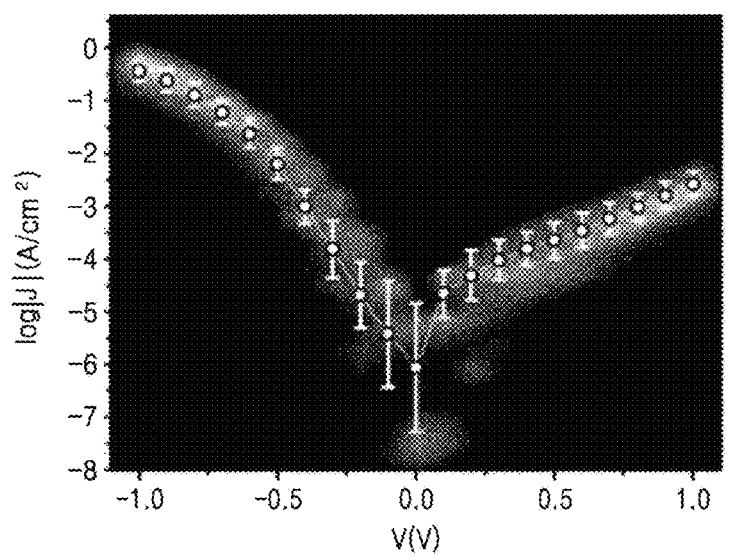

[Fig. 3]
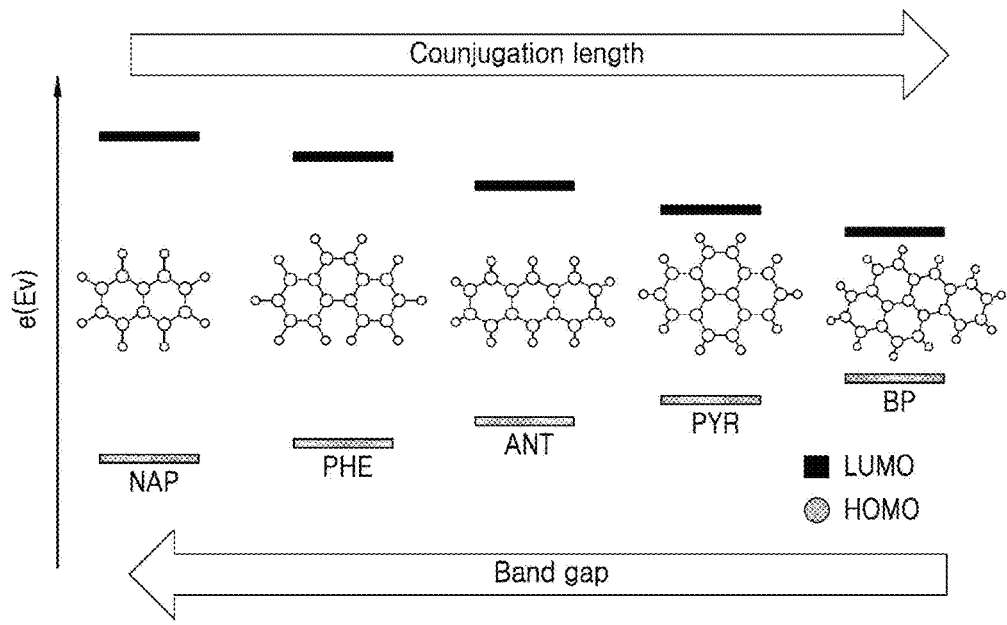
[Fig. 4]
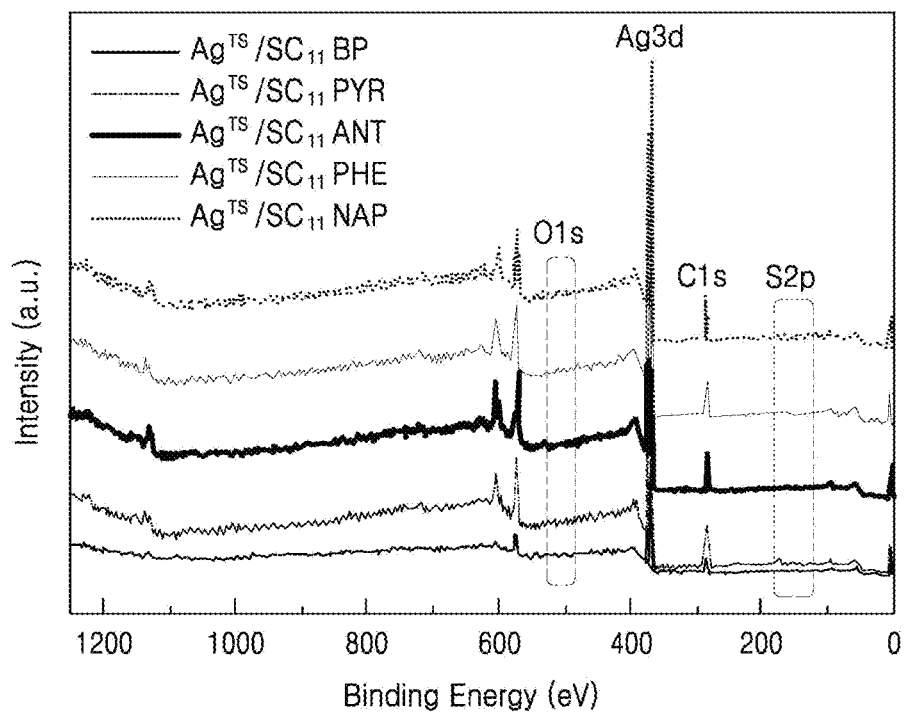

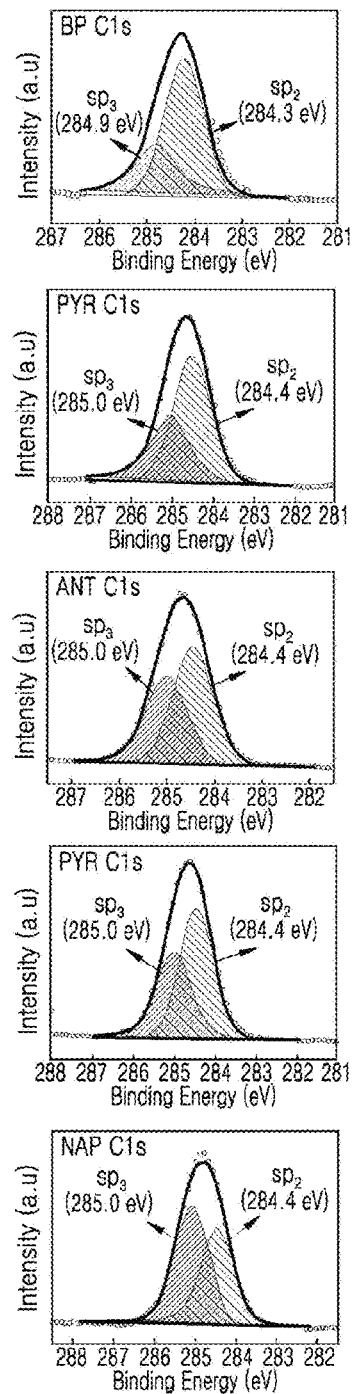
[Fig. 5]

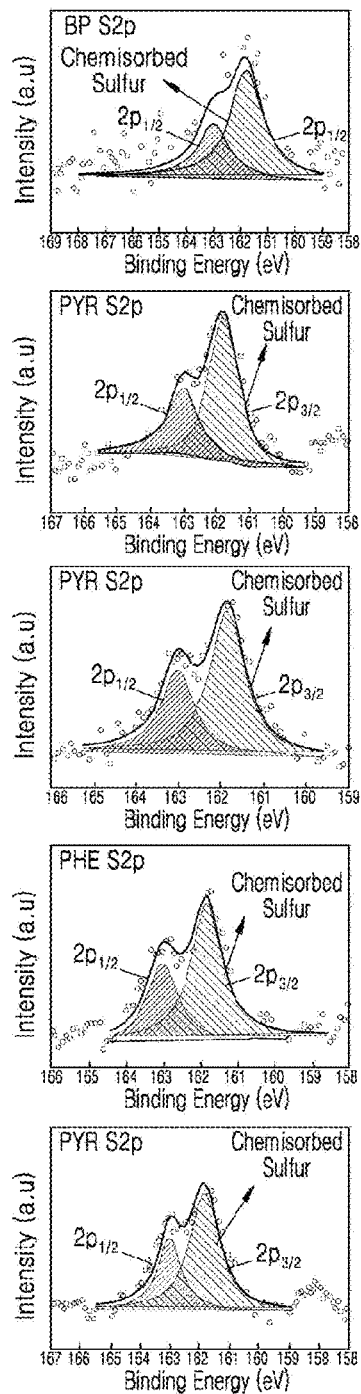
[Fig. 6]

[Fig. 7]
$Ag^{TS}$:50±43°
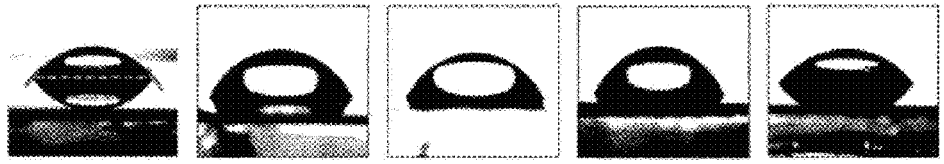
$Ag^{TS}/SC_{11}$ BP//$Ga_2O_3$/EGain:85±43°
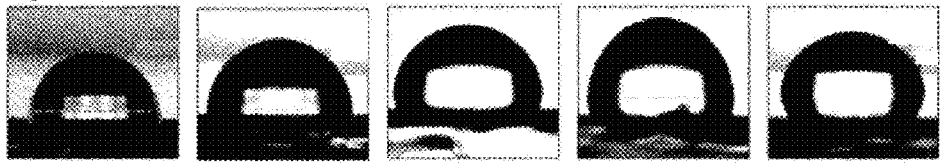
$Ag^{TS}/SC_{11}$ PYR//$Ga_2O_3$/EGain:93±3°
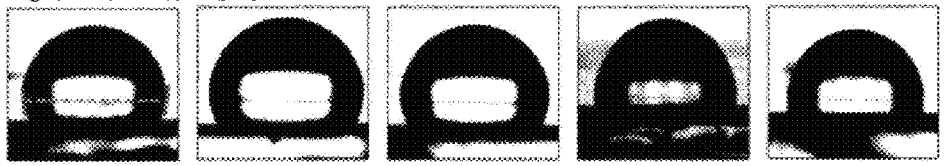
$Ag^{TS}/SC_{11}$ PHE//$Ga_2O_3$/EGain:84±2°
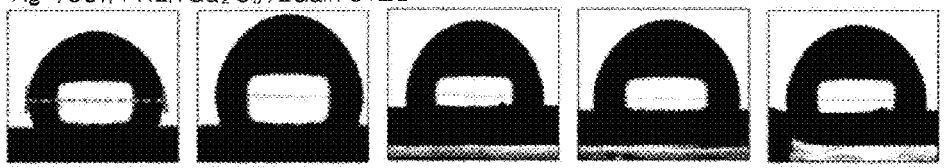
$Ag^{TS}/SC_{11}$ ANT//$Ga_2O_3$/EGain:85±1°
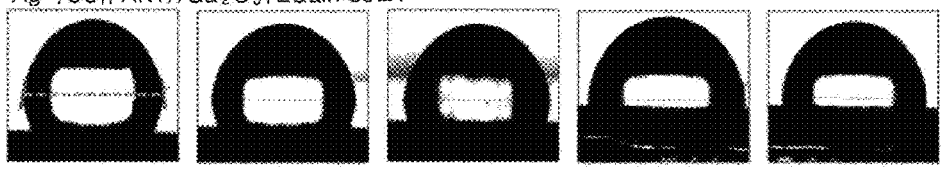
$Ag^{TS}/SC_{11}$ NAP//$Ga_2O_3$/EGain:91±3°
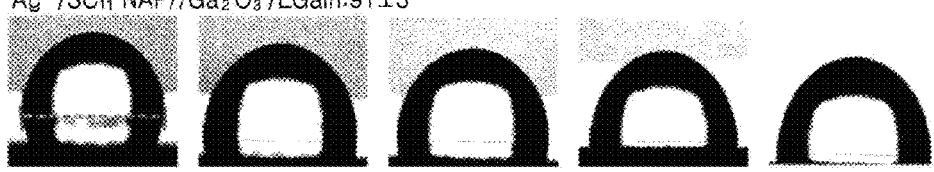

[Fig. 8]
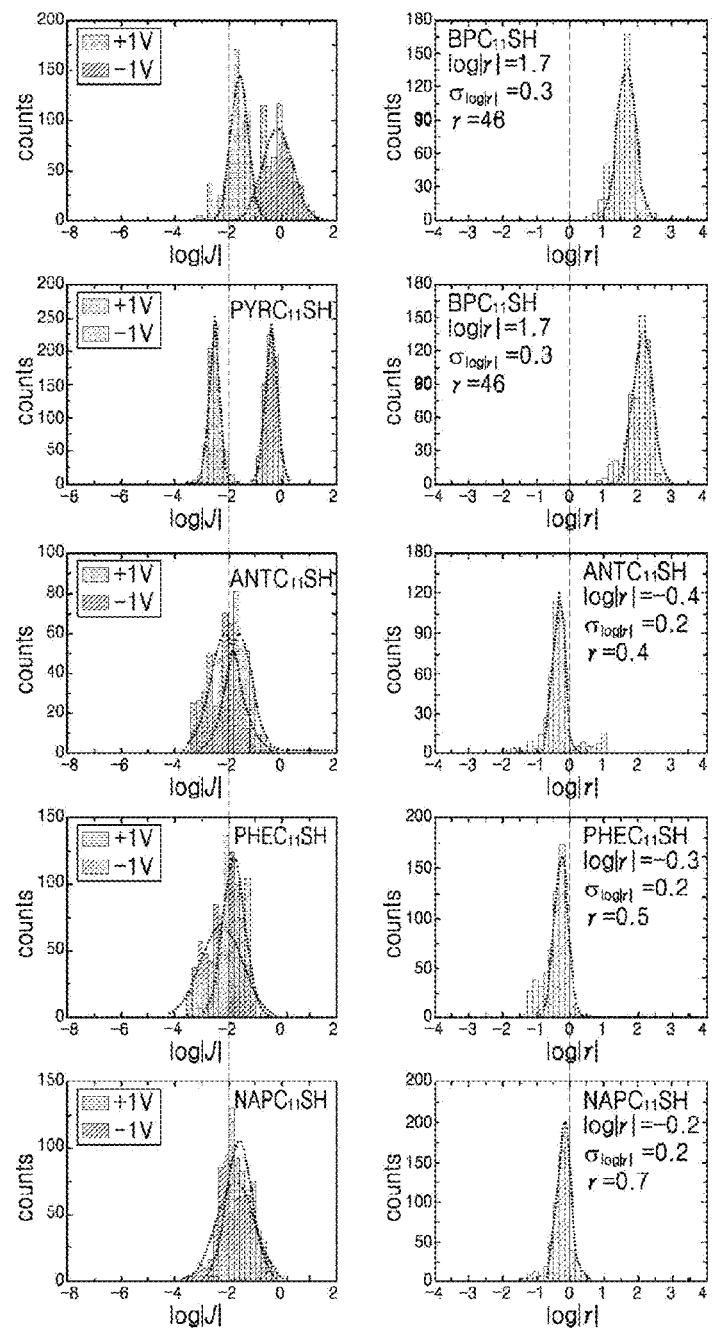

[Fig. 9]
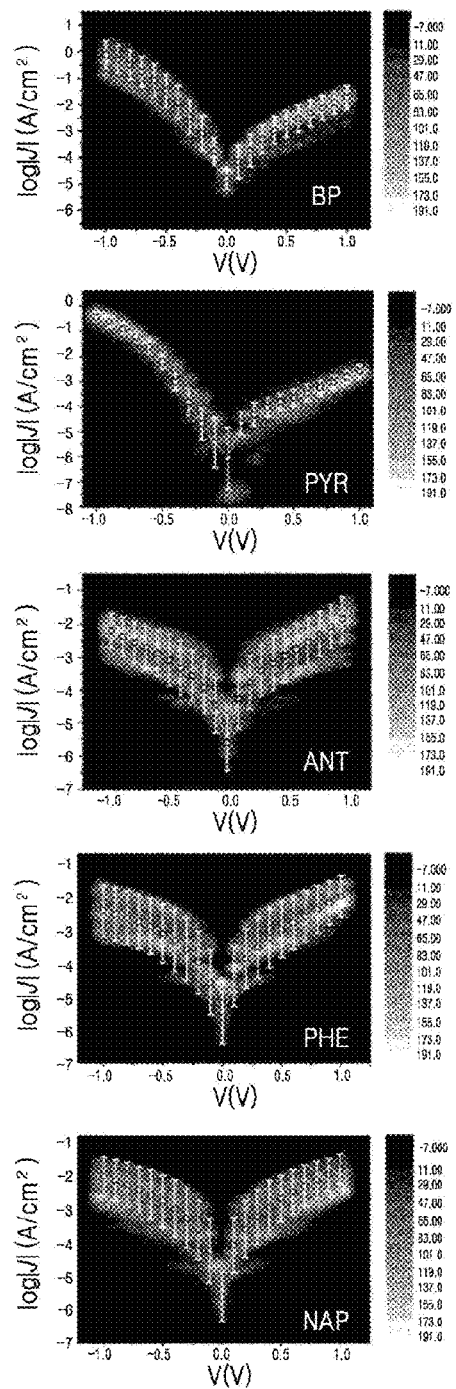

[Fig. 10]
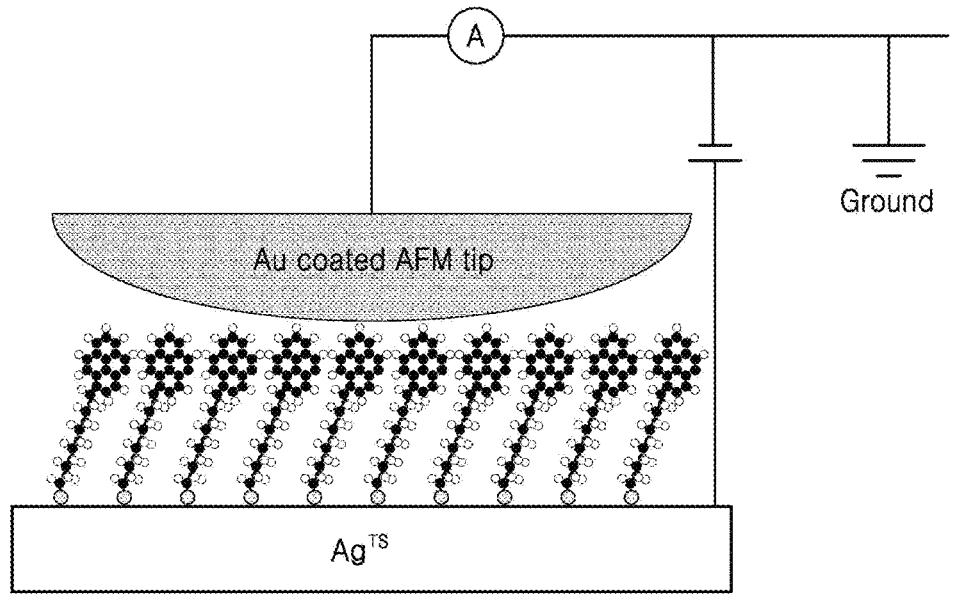
[Fig. 11]
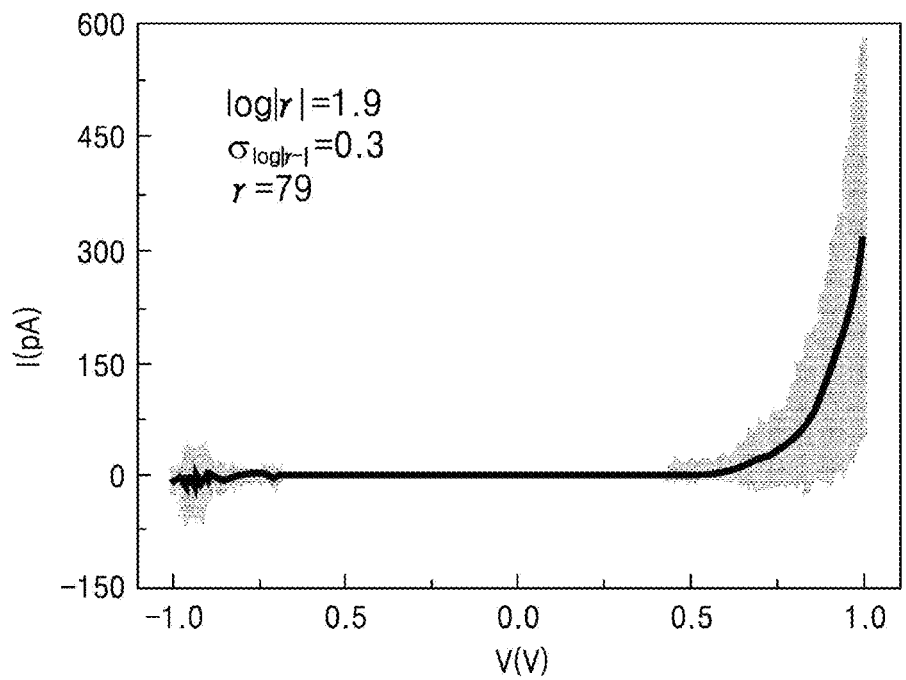

[Fig. 12]
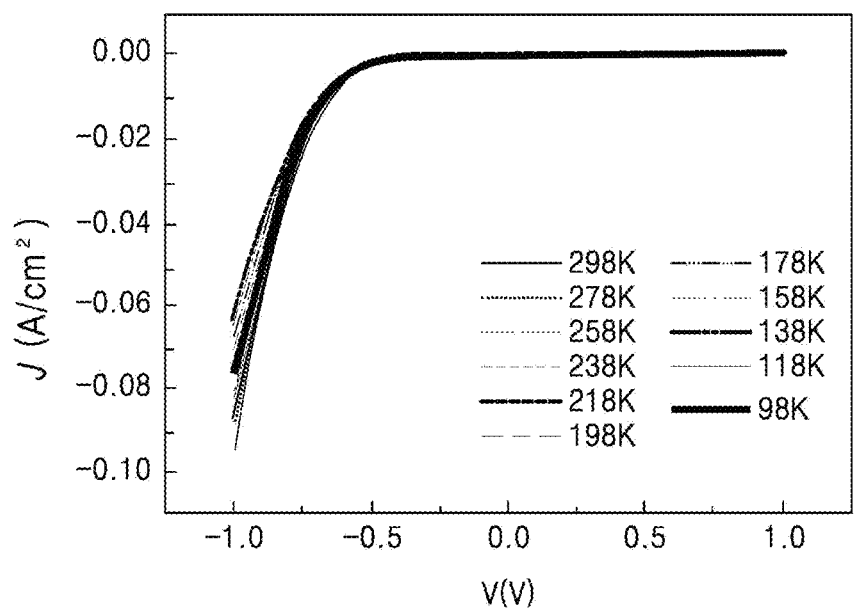
[Fig. 13]
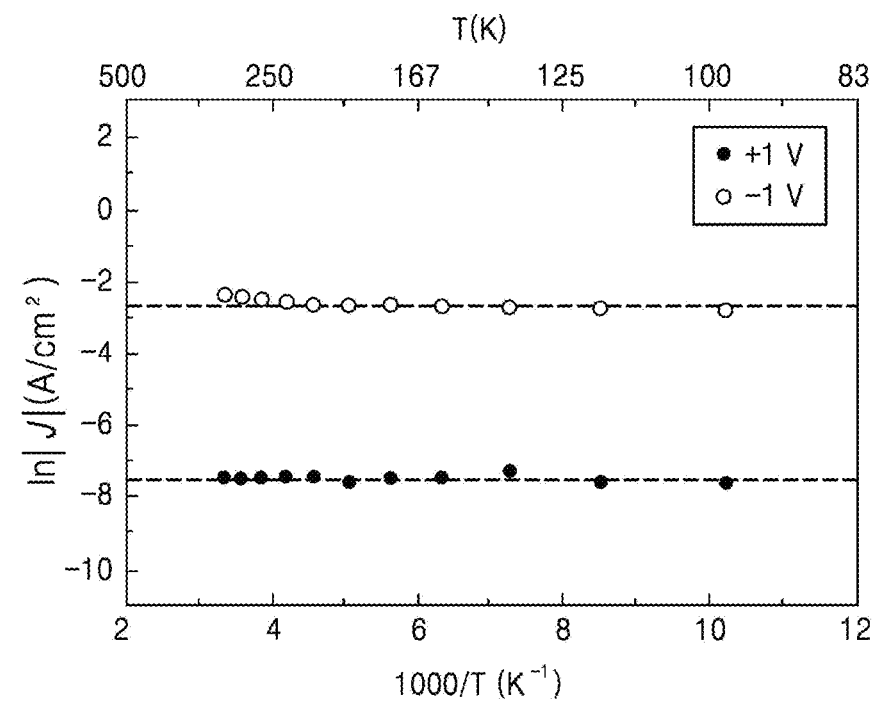

[Fig. 14]
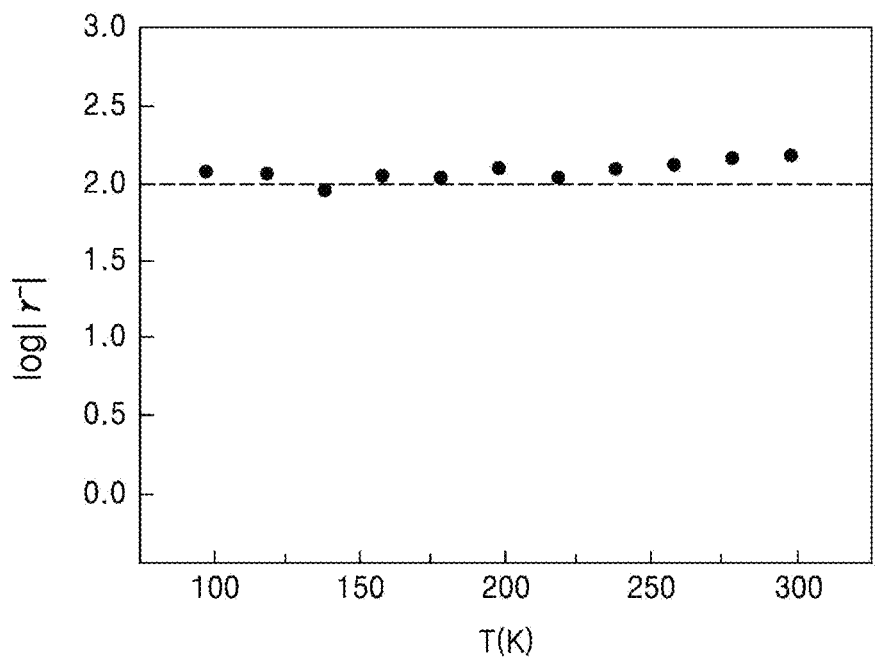
[Fig. 15]
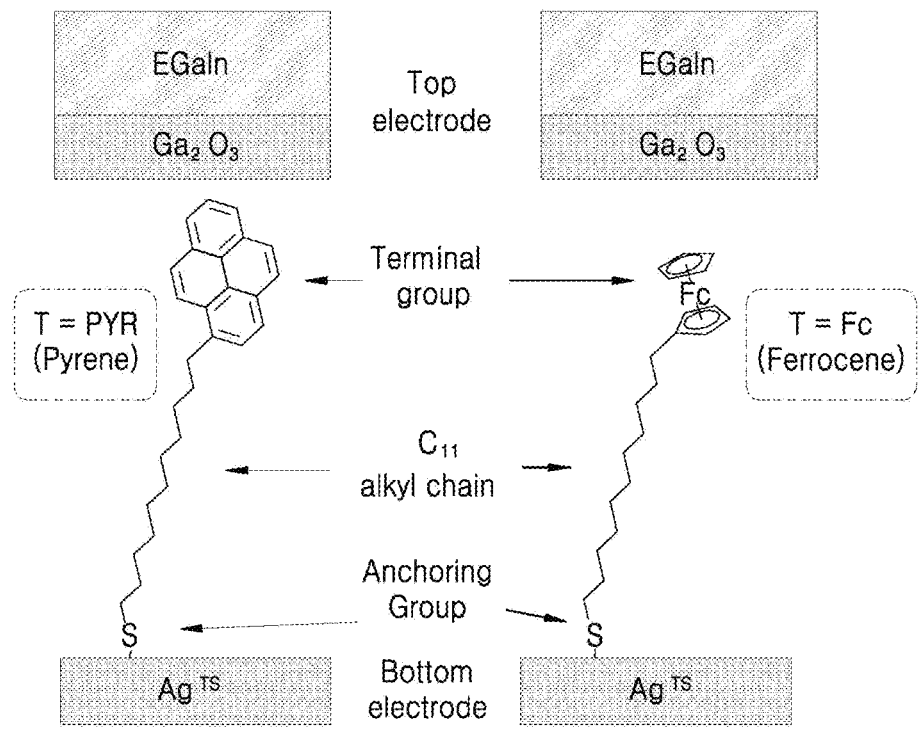

[Fig. 16]
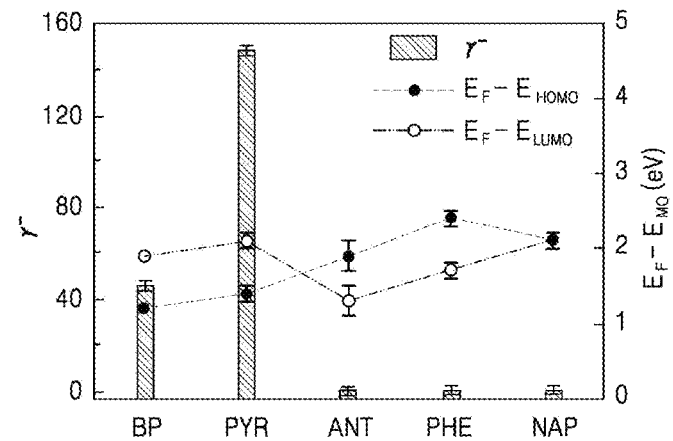
[Fig. 17]
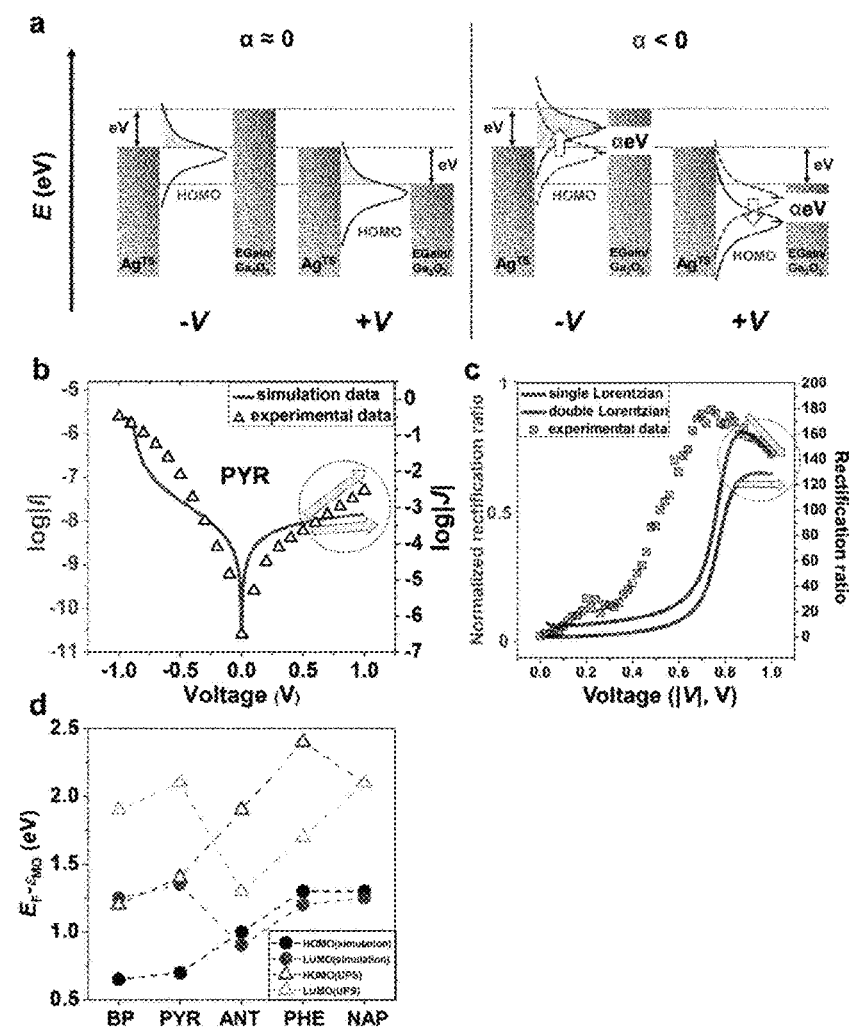

[Fig. 18]
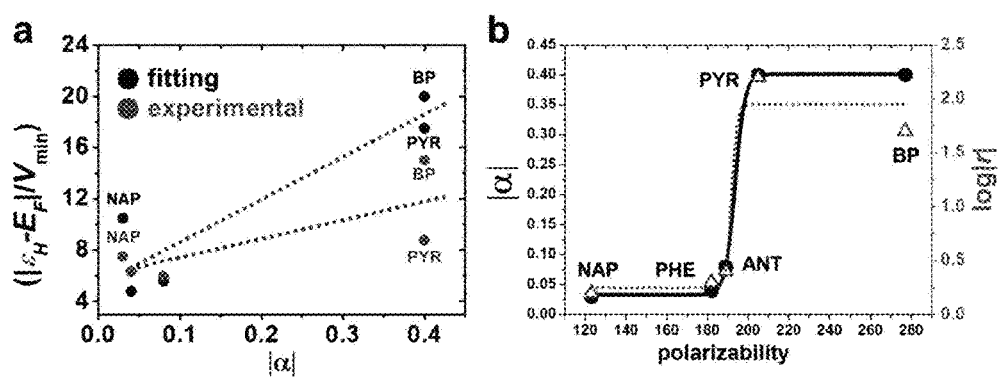

ic hydrocarbon (PAH)-terminated compound represented by Formula 1:

POLYCYCLIC AROMATIC HYDROCARBON-BASED COMPOUNDS FOR MOLECULAR ELECTRONIC DEVICE AND MOLECULAR ELECTRONIC DEVICES COMPRISING SAME

TECHNICAL FIELD

The present invention relates to a compound for a molecular electronic device and a molecular electronic device including the same. More specifically, the present invention relates to a molecular rectifying polycyclic-aromatic-hydrocarbon-terminated compound for a molecular electronic device and a molecular electronic device including a molecular layer formed by self-assembly of the compound on an electrode.

BACKGROUND ART

With the development of communication industry, computer chips playing the most important role in storing information have become highly integrated. Current semiconductor devices reach the limit of performance improvement by integration technology due to their physical limitations and high production costs. In attempts to circumvent this problem, considerable efforts have been made to fabricate molecular devices.

Molecular electronics is based on the use of individual molecules as active components for the fabrication of miniaturized functional electronic devices and requires a fundamental understanding of how the tunneling rate of charges across molecules is associated with their chemical and electronic structures.

To date, studies on the development of organic molecular materials necessary for the development of molecular electronic devices have largely focused on functional applications, including molecular wires, molecular switches, and molecular rectifiers. With the recent development of nanotechnology, such applications have been investigated and developed more and more in developed countries, particularly the United States and European countries.

Rectification refers to an electrical property widely used in electronic devices and is characterized by an asymmetric response of current to applied biases of opposite polarities. Rectification is also being investigated in molecular-scale electronic devices based on a single molecular layer or a single molecule.

Aviram and Ratner from IBM proposed for the first time in 1974 that devices with molecular diode rectifying properties can be fabricated using molecular properties. Specifically, Aviram and Ratner proposed that when electrodes are connected to both ends of molecules aligned in one direction, each of the molecules consisting of an electron donor (D), a barrier ($\sigma$), and an electron acceptor (A) (D-$\sigma$-A) such that the molecule is polarized in one direction, an electric current flows in only one direction. After this theoretical proposal, some molecular junctions including various molecular rectifiers have been reported in the literature.

Rectification in some molecular junctions is explained by biases arising from the energy barrier of quantum mechanical tunneling, potential differences between electrodes or asymmetric energy levels of molecular-electrode interfaces. Alternatively, rectification is described by the occurrence of a thermally activated hopping process at one polarity rather than at biases of opposite polarities.

The rectifying properties of most designed molecular devices have not been statistically proven and have been difficult to clearly demonstrate because the magnitudes of rectification ratios ($r^{\pm}$; $r^{+}=|J(+V)|/|J(-V)|$, $r^{-}=|J(-V)|/|J(+V)|$, where $J(V)$ is the current density at voltage V (A/cm$^2$)) are too small to say that the rectifying properties arise from the internal electronic structure of the molecules and the structure of the molecules is complex.

To solve the problem of uncertainty in this rectification mechanism, several research groups have investigated rectifiers by junction of n-alkanethiolates terminated with $\pi$-electron rich moieties such as ferrocene (Fc) and its derivatives (e.g., Fc, Fc$_2$, and Fc-C≡C-Fc), 2,2'-bipyridine (BIPY), and fullerene-C$_{60}$ with eutectic Ga—In alloy (EGaIn).

EGaIn junction technology guarantees not only convenience in fabrication and operation of junctions but also high yields of junctions to acquire statistically significant data and provides a direct advantage in performing physical organic research. Thus, the high rectification rates of these molecules have been statistically demonstrated and experimentally verified in various environments and modified structures.

n-alkanethiolates having terminal Fc derivatives exhibit rectification ratios in the range of ~10$^2$ to ~10$^5$, while n-alkanethiolates having terminal BIPY and fullerene-C$_{60}$ exhibit rectification ratios of ~10$^2$. Rectification in Fc derivatives is negative in polarity, that is, $|J(-V)|>|J(+V)|$, and the polarity of rectification in BIPY and fullerene-C$_{60}$ is opposite to that in Fc. The mechanism of rectification in Fc derivatives has been elucidated by several experiments but the criteria for rectification in BIPY and fullerene-C$_{60}$ are still not clearly established.

That is, despite many efforts around the world to develop new rectifiers based on the characteristics of organic molecules, there has not been a clear direct proof as to whether rectification of molecular electronic devices is generated according to the characteristics of organic molecules. Questions whether rectification of molecular devices using organic molecules comes from the intrinsic properties of the organic materials or occurs between two electrode metals interposing the organic molecules therebetween cannot be systematically explained at present.

Thus, there is an urgent need to develop new molecular rectifying materials that can more fundamentally explain the rectifying properties of molecular electronic devices. Nevertheless, such molecular rectifying materials are very difficult to develop. Particularly, difficult synthesis of organic molecules is recognized as a major obstacle to the development of molecular rectifying materials.

DETAILED DESCRIPTION OF THE INVENTION

Problems to be Solved by the Invention

The present invention intends to provide a novel structurally simple rectifying polycyclic-aromatic-hydrocarbon (PAH)-terminated compound for a molecular electronic device.

The present invention also intends to provide a self-assembled monolayer using the novel rectifying compound and a molecular rectifier including the self-assembled monolayer.

Means for Solving the Problems

One aspect of the present invention is to provide a structurally simple rectifying polycyclic-aromatic-hydrocarbonbon (PAH)-terminated n-alkanethiolate for a molecular electronic device, represented by Formula I:

R$_1$—(CH$_2$)$_n$—SR$_2$     [Formula I]

wherein R$_1$ is a C$_{10}$-C$_{40}$ polycyclic aromatic hydrocarbon group, R$_2$ is a hydrogen atom or a C$_1$-C$_7$ alkyl or acetyl group, and n is an integer from 1 to 20.

A further aspect of the present invention provides a molecular rectifier including a large-area tunneling junction of a self-assembled monolayer (SAM) including the compound.

Effects of the Invention

The compound of the present invention can exhibit rectifying properties when introduced between electrodes. Therefore, the compound of the present invention can be utilized as an organic material in a molecular rectifying electronic device. Particularly, the use of the compound enables the fabrication of vertically or horizontally structured molecular rectifying electronic devices or devices consisting of an array of such molecular electronic devices.

The molecular rectifier of the present invention can achieve a high rectification ratio when driven at low voltage. Therefore, the molecular rectifier of the present invention can replace a silicon-based diode device. Particularly, the molecular rectifier of the present invention is industrially applicable to wearable devices, Bluetooth devices, and IoT devices where low voltage driving is required.

In addition, the end of the compound according to the present invention is anchored to an electrode to effectively form a self-assembled molecular layer on the surface of the electrode. Due to this advantage, a molecular electronic device can be easily fabricated by placing a top electrode on the self-assembled molecular layer.

Furthermore, the basic rectifying properties of the material for the self-assembled molecular layer can be directly measured by conductive atomic force microscopy (CAFM) on the surface of the self-assembled molecular layer to clearly establish the principle of rectification.

BRIEF DESCRIPTION OF THE DRAWINGS

FIG. 1 is a schematic diagram illustrating a Ag$^{TS}$/SC$_{11}$PYR//Ga$_2$O$_3$/EGaIn junction where a self-assembled monolayer (SAM) is composed of terminal polycyclic aromatic hydrocarbon (PAH) groups (PAH=benzo[a]pyrenyl (BP), pyrenyl (PYR), anthracenyl (ANT), phenanthrenyl (PHE), and naphthyl (NAP) groups), n-alkane chains, and thiol groups as anchoring groups and van der Waals interactions are created between the PAH terminal groups and an top electrode.

FIG. 2 is a heatmap of a log|J|-V curve for a Ag$^{TS}$/SC$_{11}$PYR//Ga$_2$O$_3$/EGaIn junction, where the average rectification ratio of SC$_{11}$PYR is ~148±2.

FIG. 3 shows HOMO, LUMO and energy band gaps of PAH groups with different conjugation lengths.

FIG. 4 shows XPS spectra for Ag$^{TS}$/SC$_{11}$PAH SAMs (PAH=BP, PYR, ANT, PHE, and NAP), FIG. 5 shows C1s spectra for the SAMs, and FIG. 6 shows S2p spectra for the SAMs.

FIG. 7 shows images illustrating water contact angles for Ag$^{TS}$/SC$_{11}$PAH SAMs (PAH=BP, PYR, ANT, PHE, and NAP) (averaged from five measurements).

FIG. 8 shows histograms of log|J(V)| and log|r$^-$| for SAMs including PAH-terminated n-alkanethiols and FIG. 9 shows heatmaps of the corresponding log|J|-V traces.

FIG. 10 is a schematic diagram illustrating a nanoscale molecular junction of SC$_{11}$PYR with a Au cantilever by conductive atomic force microscopy (CAFM) and FIG. 11 shows a plot of current as a function of applied voltage (±1.0 V) measured from the CAFM junctions, where the gray region represents the standard deviation.

FIGS. 12 to 15 show the electrical properties of Ag$^{TS}$/SC$_{11}$PYR//Ga$_2$O$_3$/EGaIn under vacuum at low temperatures of 98-298 K. Specifically, FIG. 12 shows J-V traces measured at ±1.0 V, FIG. 13 shows corresponding Arrhenius plots, FIG. 14 is a log|-r$^-$| plot against temperature, and FIG. 15 shows structural similarity for EGaIn-based junctions of -PYR and -Fc rectifiers except the terminal groups (PYR vs. Fc).

FIG. 16 shows plots of energy differences between the E$_F$ of Ga$_2$O$_3$/EGaIn and the E$_{MO}$ (energy of molecular orbital (HOMO or LUMO)) of PAHs and rectification ratios for the PAH structures.

FIG. 17 shows (a) energy level diagrams illustrating the mechanism of rectification induced by the Stark shift for a HOMO conducting molecular junction, (b) a comparison of measured I-V trace for SC$_{11}$PYR SAM with the simulated one obtained by the Laudauer formula (Equation 1), (c) a comparison of measured |r$^-$|-|V| for SC$_{11}$PYR SAM with the simulated one from the data in panel (b), and (d) a comparison of HOMO and LUMO energy levels estimated by UPS with those extracted from the simulation.

FIG. 18 shows (a) a correlation between the Stark shift coefficient (|α|) and |ε-E$_F$|/V$_t$ values obtained from experimental (UPS) and fitting data and (b) polarizability of a model structure of PAHs (Values of V$_t$ were measured at -V and polarizability values were obtained from the literature).

BEST MODE FOR CARRYING OUT THE INVENTION

The present invention will now be described in more detail.

The present invention is directed to a molecular rectifying compound for a molecular electronic device, represented by Formula I:

R$_1$—(CH$_2$)$_n$—SR$_2$     [Formula I]

wherein R$_1$ is a C$_{10}$-C$_{40}$ polycyclic aromatic hydrocarbon group, R$_2$ is a hydrogen atom or a C$_1$-C$_7$ alkyl or acetyl group, and n is an integer from 1 to 20, and a molecular rectifier including the molecular rectifying compound.

According to one embodiment of the present invention, R$_1$ may be selected from pyrenyl and benzopyrenyl groups and R$_2$ may be a hydrogen atom.

As a result of identifying the characteristics of structurally simple polycyclic-aromatic-hydrocarbon (PAH)-terminated n-alkanethiolates, the inventors of the present invention have found that large-area tunnel junctions of self-assembled monolayers (SAMs) including the compounds exhibit high rectification ratios (~148±2) with a negative polarity (|J(-V)|>>|J(+V)|).

The inventors of the present invention have also conducted experiments to identify the rectifying properties of the n-alkanethiolates by changing the structure of the terminal group (PAH) from pyrenyl to naphthyl, anthracenyl, phenanthrenyl, etc. while keeping the other components of the junctions constant, experiments to measure the characteristics of the junctions at different temperatures by varying the materials for top electrodes, such as eutectic gallium-indium alloys and gold, and experiments to analyze the characteristics of the self-assembled monolayers (SAMs) by ultraviolet photoelectron spectroscopy (UPS). As a result of the experiments, the inventors have found that rectification is associated with the HOMO energy level of the PAH and relies on pure tunneling rather than on thermally activated hopping. The inventors have also found that the Stark effect is a major factor that determines the molecular rectification of the compound represented by Formula I.

According to one embodiment of the present invention, the molecular rectifier rectifies the tunneling current density to a significant level in a self-assembled monolayer (SAM)-based large-area junction having a $Ag^{TS}/SC_{11}PYR//Ga_2O_3/$EGaIn structure using the compound represented by Formula I.

As shown in FIG. 1, $Ag^{TS}$ is a silver (Ag) electrode prepared by template-stripping (TS), $SC_{11}PYR$ is the n-alkanethiolate of the present invention having a pyrenyl group (PYR) as a terminal polycyclic aromatic hydrocarbon (PAH) group, $Ga_2O_3$/EGaIn is a eutectic gallium-indium alloy electrode covered with $Ga_2O_3$ layers, and // indicates a van der Waals interaction region.

As shown in FIG. 2, the rectification ratio is ~148±2 and has a negative polarity ($|J(-V)|\gg|J(+V)|$).

In the Examples section that follows, the following experiments were performed and the results were analyzed to clearly demonstrate the rectifying properties of the inventive compounds.

(i) An experiment was conducted to investigate the relationship between the rectifying properties of the inventive compounds having different terminal PAH groups with different conjugation lengths (for example, benzo[a]pyrenyl (BP), pyrenyl (PYR), anthracenyl (ANT), phenanthrenyl (PHE), and naphthyl (NAP) groups) and the frontier orbital energy levels of the PAH groups.

(ii) A low temperature experiment was conducted to determine whether a thermally activated hopping process contributes to the rectifying properties of conventional ferrocene (Fc)-terminated organometallic n-alkanethiolates.

(iii) An experiment was conducted to evaluate whether the redox activity of the $Ga_2O_3$ layer or the specific Fermi level ($E_F$) of EGaIn plays a role in rectification by replacing the top electrode with a gold electrode using conductive atomic force microscopy (CAFM) and measuring J-V traces from the similar junction including the gold top electrode.

(iv) An experiment was conducted to confirm the HOMO and LUMO levels of the PAH groups by ultraviolet photoelectron spectroscopy (UPS) and the relationship between the PAH groups and rectification.

(v) It was found that the rectifying properties were not attributed to the redox properties of $Ga_2O_3$ at the interface with the top electrode.

(vi) It was also found that the Stark effect is a major factor that determines the molecular rectification of the inventive compounds.

MODE FOR CARRYING OUT THE INVENTION

The present invention will be explained in more detail with reference to the following examples, including experimental examples. These examples are provided for illustrative purposes only and the scope of the invention is not limited thereto.

All reagents were purchased from Sigma-Aldrich, Alfa Aesar, and TCI and used as supplied unless otherwise specified. All organic solvents were purchased from Sigma-Aldrich and Daejung while water was purified using an Aqua MAX-Basic System (deionized water, the electrical resistivity of which is ≤18.2 MΩcm). High purity eutectic gallium-indium (EGaIn; 99.99%) was obtained from Sigma-Aldrich and used as supplied. Polycyclic-aromatic-hydrocarbon-terminated n-alkanethiols were synthesized and stored under nitrogen atmosphere at ≤4° C. Silver thin films (300 nm) were deposited onto silicon wafer (100 mm in diameter; 1-10 Ωcm, 525±50 microns thick) by e-beam evaporator (ULVAC). Photo-curable polymer was purchased from Norland (NOA81) and used as supplied.

$^1H$ and $^{13}C$ NMR spectra were recorded on a Bruker FT-NMR Advance-500 using $CDCl_3$ as a solvent and residual solvents as an internal standard. Chemical shifts are expressed in parts per million (ppm) related to internal TMS and coupling constants (J) are in Hertz. MS (ESI-QTOF) measurements were recorded on a Bruker compat Q-TOF MS. All XPS and UPS measurements were carried out on a Thermo Thetaprobe with a monochromated Al Kα and He I source. Junction measurements at variable temperatures were carried out in a cryogenic probe station (PS-CG2ST, MODUSYS).

SYNTHESIS EXAMPLES: SYNTHESIS OF POLYCYCLIC-AROMATIC-HYDROCARBON (PAH)-TERMINATED N-ALKANETHIOLS

Synthesis Example 1: Synthesis of 11-(pyren-1-yl)undecane-1-thiol S4

11-(Pyren-1-yl)undecane-1-thiol S4 was synthesized following Scheme 1:

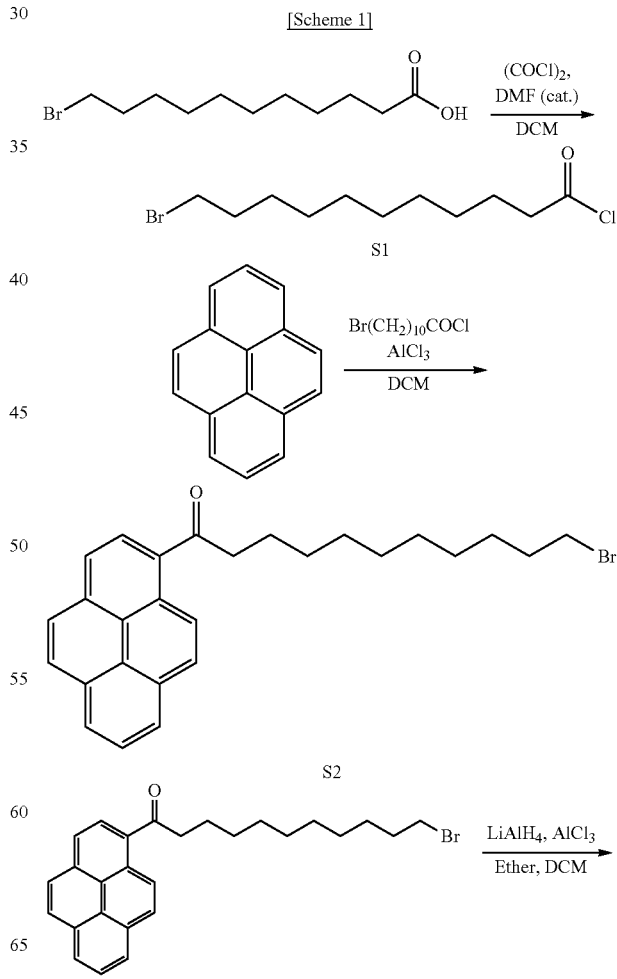

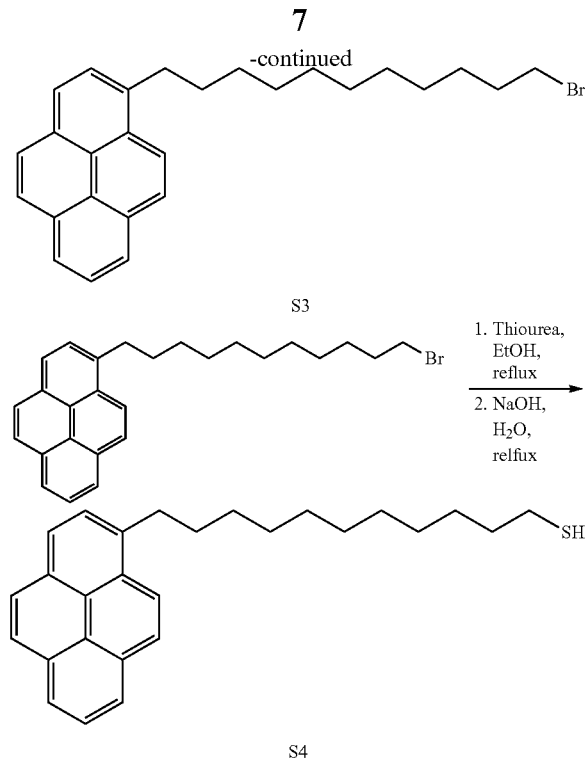

(1) Synthesis of I1-bromoundecanoyl chloride S1

11-Bromoundecanoyl chloride (1 g, 3.77 mmol) and DMF (0.03 mL, 0.38 mmol) were dissolved in anhydrous DCM (10 mL) in a 50 mL round bottom flask. A solution of oxalyl chloride (0.80 mL, 9.43 mmol) was added dropwise to the flask. The mixture was stirred for another 30 min. The solvent and excess oxalyl chloride were removed under vacuum with an oil pump equipped with a cold trap. The compound was used for the next step without purification.

(2) Synthesis of 11-bromo-1-(pyren-1-yl)undecan-1-one S2

S1 and AlCl$_3$ (0.60 g, 4.51 mmol) were dissolved in 10 mL of anhydrous DCM and cooled to 0° C. in an ice bath. To the solution was added dropwise a solution of pyrene (0.76 g, 3.76 mmol) in 10 mL of DCM. The mixture was stirred at 0° C. for 5 h. The reaction mixture was poured into an ice/water/Et$_2$O mixture. The organic layer was washed three times with water and dried over MgSO$_4$. The crude product was purified by silica gel chromatography using hexane/DCM (2:1) as the eluent. S2 was obtained as a white solid in a yield of 61%.

$^1$H NMR (CDCl$_3$, 500 MHz, 25° C.): δ 8.85 (d, 1H, J=9.3 Hz, Ar); 8.05-8.33 (m, 8H, Ar); 3.39 (t, 2H, J=6.9 Hz); 3.22 (t, 2H, J=7.5 Hz); 1.85 (m, 4H); 1.28-1.45 (m, 12H, aliphatic chain).

$^{13}$C NMR (CDCl$_3$, 500 MHz, 25° C.): δ 205.47, 133.58, 132.99, 131.12, 130.60, 129.47, 129.39, 129.25, 127.11, 126.39, 126.19, 125.99, 125.97, 125.05, 124.83, 124.39, 124.02, 42.71, 34.06, 32.83, 29.44, 29.39, 29.36, 28.74, 28.16, 25.01.

MS (ESI) m/z: [M+Na]$^+$ calcd. for C$_{27}$H$_{29}$BrONa: 471.1300; found: 471.1297.

(3) Synthesis of 1-(11-bromoundecyl)pyrene S3

A solution of AlCl$_3$ (0.77 g, 5.74 mmol) in 5 mL of dry Et$_2$O was added dropwise to a 1 M solution of LiAlH$_4$ in dry Et$_2$O in a round bottom flask. Then, the mixture was cooled to 0° C. in an ice bath and a solution of S2 (1.04 g, 2.3 mmol) in 10 mL of dry DCM was added dropwise thereto. The resulting mixture was stirred at room temperature and the reaction was monitored by TLC until S2 disappeared. The reaction was quenched by the addition of 10 mL of Et$_2$O and 10 mL of water. The organic layer was extracted with DCM and dried over MgSO$_4$. The crude product was purified by silica gel column chromatography (eluent: 10% DCM in hexane (v/v)), affording S3 in a yield of 60%.

$^1$H NMR (CDCl$_3$, 500 MHz, 25° C.): δ 7.86-8.30 (m, 9H, Ar); 3.40 (t, 2H, J=6.9 Hz); 3.34 (m, 2H); 1.85 (sxt, 4H, J=7.4 Hz); 1.28-1.51 (m, 14H, aliphatic chain).

$^{13}$C NMR (CDCl$_3$, 500 MHz, 25° C.): δ 137.35, 131.47, 130.96, 129.69, 128.62, 127.55, 127.27, 127.09, 126.49, 125.76, 125.10, 125.08, 124.77, 123.55, 34.07, 33.63, 32.85, 31.95, 29.80, 29.56, 29.52, 29.42, 28.75, 28.18.

MS (ESI) m/z: [M+Na]$^+$ calcd. for C$_{27}$H$_{31}$BrNa: 457.1507; found: 457.1503.

(4) Synthesis of 11-(pyren-1-yl)undecane-1-thiol S4

A mixture of S3 (0.58 g, 1.33 mmol) and thiourea (0.11 g, 1.47 mmol) in 20 mL of anhydrous EtOH was refluxed in a 50 mL round bottom flask equipped with a reflux condenser for 24 h. To the solution was added an aqueous solution of NaOH (0.11 g, 2.66 mmol). The resulting solution was refluxed under N$_2$ for 1 h. The reaction mixture was cooled to room temperature under N$_2$ and extracted with DCM. The combined organic layer was dried over Na$_2$SO$_4$ and concentrated in vacuo. The crude product was purified by silica gel column chromatography (eluent: 20% DCM in hexane (v/v), solvents were degassed by bubbling N$_2$ for 10 min.), affording S4 in a yield of 50%.

$^1$H NMR (CDCl$_3$, 500 MHz, 25° C.): δ 7.86-8.29 (m, 9H, Ar); 3.34 (m, 2H); 2.50 (q, 2H, J=7.4 Hz); 1.85 (dt, 2H, J=15.3, 7.7 Hz); 1.27-1.62 (m, 16H, aliphatic chain).

$^{13}$C NMR (CDCl$_3$, 500 MHz, 25° C.): δ 137.36, 131.47, 130.96, 129.69, 128.62, 127.55, 127.26, 127.08, 126.48, 125.76, 125.10, 124.77, 124.61, 123.55, 34.05, 33.63, 31.96, 29.81, 29.58, 29.50, 29.06, 28.38, 24.67.

MS (ESI) m/z: [M+Na]$^+$ calcd. for C$_{27}$H$_{32}$SNa: 411.2117; found: 411.2119.

Synthesis Example 2: Synthesis of 11-(phenanthren-9-yl)undecane-1-thiol S6

11-(Phenanthren-9-yl)undecane-1-thiol S6 was synthesized following Scheme 2:

[Scheme 2]

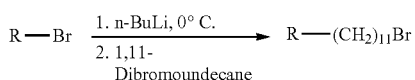

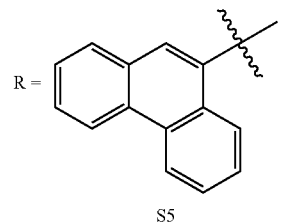

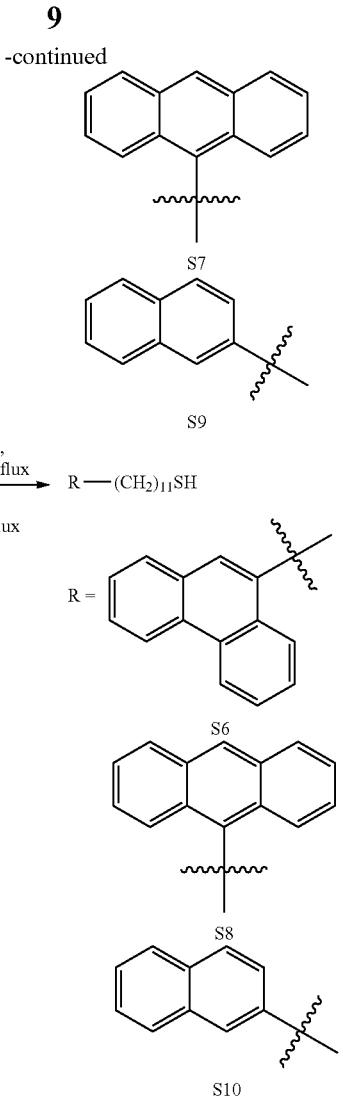

(1) Synthesis of 9-(11-bromoundecyl)phenanthrene S5

A solution of 9-bromophenanthrene (0.61 g, 3.43 mmol) in dry ether (10 mL) was mixed with n-butyllithium (1.17 mL, 2.5 M in hexane, 1.5 eq.) under a $N_2$ atmosphere at 0° C. After stirring at room temperature for 30 min, 1,11-dibromoundecane (1.83 g, 5.83 mmol) was added at once to the reaction mixture. The resulting mixture was further refluxed for 2 h. The reaction solution was then cooled to room temperature and partitioned between DCM and water. The aqueous layer was extracted with DCM, the combined organic layer was dried over $MgSO_4$, the mixture was filtered, and the solvent was evaporated from the filtrate. The crude product was purified by column chromatography (hexane:EA=9:1), affording S5 in a yield of 26%.

$^1$H NMR (CDCl$_3$, 500 MHz, 25° C.): δ 8.75 (m, 1H, Ar); 8.65 (m, 1H, Ar); 8.10 (m, 1H, Ar); 7.82 (m, 1H, Ar); 7.55-7.67 (m, 5H, Ar); 3.40 (t, 2H, J=6.9 Hz); 3.11 (m, 2H); 1.79-1.88 (m, 4H); 1.29-1.51 (m, 14H, aliphatic chain).

$^{13}$C NMR (CDCl$_3$, 500 MHz, 25° C.): δ 136.99, 131.97, 131.36, 130.71, 129.61, 128.00, 126.56, 126.44, 126.05, 125.94, 125.83, 124.49, 123.21, 122.43, 34.05, 33.50, 32.85, 30.26, 29.85, 29.58, 29.55, 29.53, 29.42, 28.76, 28.18.

MS (ESI) m/z: [M+Na]$^+$ calcd. for C$_{25}$H$_{31}$BrNa: 433.1501; found: 433.1505.

(2) Synthesis of 11-(phenanthren-9-yl)undecane-1-thiol S6

11-(Phenanthren-9-yl)undecane-1-thiol S6 was synthesized following Scheme 2 and the synthetic procedure described for S4.

$^1$H NMR (CDCl$_3$, 500 MHz, 25° C.): δ 8.73 (m, 1H, Ar); 8.65 (d, 1H, J=7.9 Hz, Ar); 8.10 (m, 1H, Ar); 7.82 (m, 1H, Ar); 7.55-7.67 (m, 5H, Ar); 3.11 (t, 2H); 2.51 (q, 2H, J=7.4 Hz); 1.82 (dt, 2H, J=15.4, 7.6 Hz); 1.60 (quin, 2H, J=7.4 Hz); 1.28-1.51 (m, 14H, aliphatic chain).

$^{13}$C NMR (CDCl$_3$, 500 MHz, 25° C.): δ 137.00, 131.98, 131.37, 130.72, 129.61, 128.00, 126.55, 126.43, 126.05, 125.94, 125.82, 124.49, 123.20, 122.43, 34.05, 33.49, 30.26, 29.86, 29.60, 29.58, 29.55, 29.50, 29.06, 28.38, 24.66.

MS (ESI) m/z: [M+Na]$^+$ calcd. for C$_{25}$H$_{32}$SNa: 387.2117; found: 387.2119.

Synthesis Example 3: Synthesis of 11-(anthracen-9-yl)undecane-1-thiol S8

11-(Anthracen-9-yl)undecane-1-thiol S8 was synthesized following Scheme 2.

(1) Synthesis of 9-(11-bromoundecyl)anthracene S7

9-(11-Bromoundecyl)anthracene S7 was synthesized following Scheme 2 and the synthetic procedure described for S5.

$^1$H NMR (CDCl$_3$, 500 MHz, 25° C.): δ 8.33 (s, 1H, Ar); 8.25 (d, 2H, J=9 Hz, Ar); 7.99 (d, 2H, J=8.4 Hz, Ar); 7.48 (m, 4H, Ar); 3.60 (m, 2H); 3.41 (t, 2H, J=6.9 Hz); 1.83 (m, 4H); 1.58 (dt, 2H, J=15.2, 7.4 Hz); 1.30-1.44 (m, 14H, aliphatic chain).

$^{13}$C NMR (CDCl$_3$, 500 MHz, 25° C.): δ 135.49, 131.66, 129.53, 129.19, 125.46, 125.31, 124.77, 124.49, 34.05, 32.85, 31.41, 30.35, 29.61, 29.59, 29.53, 29.43, 28.76, 28.18, 28.10.

MS (ESI) m/z: [M+Na]$^+$ calcd. for C$_{27}$H$_{31}$BrNa: 433.1501; found: 433.1505.

(2) Synthesis of 11-(anthracen-9-yl)undecane-1-thiol S8

11-(Anthracen-9-yl)undecane-1-thiol S8 was synthesized following Scheme 2 and the synthetic procedure described for S4.

$^1$H NMR (CDCl$_3$, 500 MHz, 25° C.): δ 8.33 (s, 1H, Ar); 8.26 (d, 2H, J=9 Hz, Ar); 8.00 (d, 2H, J=8.2 Hz, Ar); 7.48 (m, 4H, Ar); 3.60 (m, 2H); 2.52 (q, 2H, J=7.5 Hz); 1.81 (dt, 2H, J=5.8, 7.9 Hz); 1.59 (m, 4H); 1.29-1.42 (m, 12H, aliphatic chain).

$^{13}$C NMR (CDCl$_3$, 500 MHz, 25° C.): δ 135.51, 131.66, 129.53, 129.19, 125.46, 125.31, 124.77, 124.49, 34.06, 31.42, 30.36, 29.63, 29.60, 29.58, 29.51, 29.07, 28.38, 28.10, 24.67.

MS (ESI) m/z: [M+Na]$^+$ calcd. for C$_{27}$H$_{31}$BrNa: 387.2117; found: 387.2117.

Synthesis Example 4: Synthesis of 11-(naphthalen-2-yl)undecane-1-thiol S10

11-(Naphthalen-2-yl)undecane-1-thiol S10 was synthesized following Scheme 2.

(1) Synthesis of 12-(11-bromoundecyl)naphthalene S9

S9 was synthesized following Scheme 2 and the synthetic procedure described for S5.

$^1$H NMR (CDCl$_3$, 500 MHz, 25° C.): δ 7.75-7.81 (m, 3H, Ar); 7.61 (s, 1H, Ar); 7.39-7.47 (m, 2H, Ar); 7.33 (dd, 1H, J=8.4, 1.8 Hz, Ar); 3.40 (t, 2H, J=6.9 Hz); 2.76 (m, 2H); 1.84 (m, 2H); 1.70 (m, 2H); 1.27-1.42 (m, 14H, aliphatic chain).

$^{13}$C NMR (CDCl$_3$, 500 MHz, 25° C.): δ 140.46, 133.64, 131.92, 127.72, 127.61, 127.47, 127.40, 126.29, 125.81, 124.99, 36.13, 34.10, 32.85, 31.39, 29.53, 29.43, 29.33, 28.77, 28.19.

(2) Synthesis of 11-(naphthalen-2-yl)undecane-1-thiol S10

11-(Naphthalen-2-yl)undecane-1-thiol S10 was synthesized following Scheme 2 and the synthetic procedure described for S4.

$^1$H NMR (CDCl$_3$, 500 MHz, 25° C.): δ 7.75-7.81 (m, 3H, Ar); 7.61 (s, 1H, Ar); 7.39-7.47 (m, 2H, Ar); 7.33 (dd, 1H, J=8.4 Hz); 2.76 (m, 2H); 2.52 (q, 2H, J=7.5 Hz); 1.70 (quin, 2H, J=7.5 Hz); 1.6 (quin, 2H, J=7.4 Hz); 1.27-1.38 (m, 14H, aliphatic chain).

$^{13}$C NMR (CDCl$_3$, 500 MHz, 25° C.): δ 140.48, 133.63, 131.92, 127.71, 127.60, 127.46, 127.40, 126.28, 125.81, 124.98, 36.13, 34.07, 31.39, 29.56, 29.53, 29.51, 29.34, 29.08, 28.39, 24.68.

MS (ESI) m/z: [M+Na]$^+$ calcd. for C$_{27}$H$_{31}$BrNa: 337.1960; found: 337.1963.

Synthesis Example 5: Synthesis of 11-(benzo[a]pyren-6-yl)undecane-1-thiol S14

11-(Benzo[a]pyren-6-yl)undecane-1-thiol S14 was synthesized following Scheme 3.

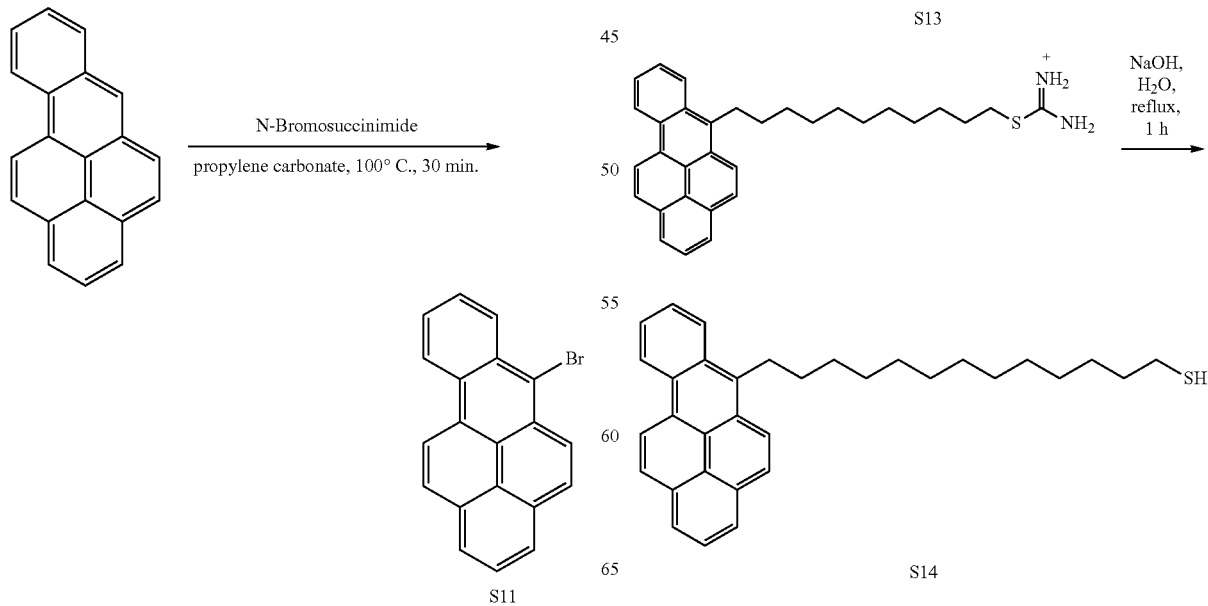

(1) Synthesis of 6-bromobenzo[a]pyrene S11

N-Bromosuccinimide (0.64 g, 3.6 mmol) was added to benzo[a]pyrene (1 g, 3.96 mmol) in propylene carbonate (20 mL). The mixture was maintained at 100° C. for 30 min and an equal volume of water was added thereto. The reaction mixture was extracted with DCM and residual solvents were evaporated. The crude product was purified by recrystallization from acetone and washed with EtOH, affording S11 in a yield of 77%.

$^1$H NMR (CDCl$_3$, 500 MHz, 25° C.): δ 9.05 (m, 2H); 8.88 (m, 1H); 8.57 (d, 1H, J=9.3 Hz); 8.34 (d, 1H, J=9.2 Hz); 8.26 (d, 1H, J=7.6); 8.14 (d, 1H, J=7.2 Hz); 8.02 (m, 2H); 7.88 (m, 2H).

$^{13}$C NMR (CDCl$_3$, 500 MHz, 25° C.): δ 131.42, 131.04, 130.05, 129.75, 128.92, 128.84, 128.70, 127.99, 127.48, 127.36, 127.13, 126.51, 126.46, 126.39, 125.58, 124.59, 124.36, 123.16, 122.07, 121.58.

MS (ESI) m/z: [M] calcd. for C$_{20}$H$_{11}$Br: 330.0044; found: 330.0040.

(2) Synthesis of 6-(11-bromoundecyl)benzo[a]pyrene S12

S12 was synthesized following the synthetic procedure described for S5 and used for the next step without purification.

$^1$H NMR (CDCl$_3$, 500 MHz, 25° C.): δ 9.11 (m, 1H, Ar); 9.05 (d, 1H, J=9.3 Hz, Ar); 8.57 (m, 1H, Ar); 8.28 (m, 2H, Ar); 8.21 (d, 1H, J=7.5 Hz, Ar); 8.06 (d, 1H, J=6.9 Hz, Ar); 7.96 (m, 2H, Ar); 7.83 (m, 2H, Ar); 3.74 (m, 2H); 3.41 (t, 2H, J=6.9 Hz); 1.88 (m, 4H); 1.64 (dt, 2H, J=15.2, 7.5 Hz); 1.26-1.42 (m, 12H, aliphatic chain).

$^{13}$C NMR (CDCl$_3$, 500 MHz, 25° C.): δ 133.99, 131.60, 131.28, 129.82, 128.28, 127.79, 126.97, 126.77, 126.24, 126.07, 126.00, 125.62, 125.52, 125.50, 125.05, 124.62, 124.46, 123.90, 123.60, 122.19, 34.15, 32.86, 31.58, 30.39, 29.66, 29.57, 29.47, 28.79, 28.61, 28.20.

(3) Synthesis of 11-(benzo[a]pyren-6-yl)undecane-1-thiol S13

A mixture of S12 (0.11 g, 0.23 mmol) and thiourea (0.034 g, 0.45 mmol) in 20 mL of anhydrous EtOH was refluxed in a 50 mL round bottom flask equipped with a reflux condenser for 24 h. The crude product was purified by column chromatography (DCM→50% MeOH in DCM (v/v)) to give pure thiouronium salt in a yield of 41%.

A solution of the thiouronium salt (0.054 g, 0.096 mmol) in 20 mL of anhydrous EtOH was refluxed and an aqueous solution of NaOH (7 mg, 0.19 mmol) was added thereto. The mixture was refluxed under N$_2$ for 1 h. The reaction mixture was cooled to room temperature under N$_2$ and extracted with DCM. The combined organic layer was dried over Na$_2$SO$_4$ and concentrated in vacuo. The crude product was purified by silica gel column chromatography (eluent: 10% DCM in hexane (v/v), solvents were degassed by bubbling N$_2$ for 10 min.), affording S13 in a yield of 33%.

$^1$H NMR (CDCl$_3$, 500 MHz, 25° C.): δ 9.11 (m, 1H, Ar); 9.05 (d, 1H, J=9.2 Hz, Ar); 8.57 (m, 1H, Ar); 8.28 (m, 2H, Ar); 8.20 (d, 1H, J=7.8 Hz); 8.06 (d, 1H, J=6.9 Hz); 7.96 (m, 2H, Ar); 7.93 (m, 2H, Ar); 3.74 (m, 2H); 2.52 (q, 2H, J=7.4 Hz); 1.91 (dt, 2H, J=15.7, 8 Hz); 1.63 (m, 4H); 1.29-1.47 (m, 12H, aliphatic chain).

$^{13}$C NMR (CDCl$_3$, 500 MHz, 25° C.): δ 133.99. 131.60, 131.28, 129.82, 128.28, 127.79, 126.96, 126.75, 126.23, 126.07, 125.99, 125.62, 125.51, 125.49, 125.04, 124.62, 124.46, 123.89, 123.60, 122.17, 34.10, 31.59, 30.40, 29.68, 29.66, 29.63, 29.55, 29.10, 28.61, 28.41, 24.71.

MS (ESI) m/z: [M+Na]$^+$ calcd. for C$_{31}$H$_{34}$S: 461.2279; found: 461.2272.

Examples: Preparation of Self-Assembled Monolayers (SAMs) and Ag$^{TS}$/SC$_{11}$PYR//Ga$_2$O$_3$/EGaIn Junctions Each of S4, S6, S8, S10 and S14 prepared in Synthesis Examples 1-5 was dissolved in toluene (anhydrous 99.9%) until a total concentration of 3 mM was reached. The solution was placed in a vial, sealed, and degassed by bubbling N$_2$ for ca. 10 min. A template-stripped silver (Ag$^{TS}$) (or gold, Au$^{TS}$) chip was rinsed with pure toluene and placed in the solution with the exposed metal face up. The vial was then filled with N$_2$. After 1-3 h incubation at room temperature, the SAM-bound Ag$^{TS}$ chip was removed from the solution and rinsed by repeatedly dipping the chip into clean toluene (3×1 mL). The solvent on the SAM was evaporated in air for a few seconds.

All junction formation and measurements were carried out in ambient conditions. After a SAM was brought into contact with an electrode, a conical tip of EGaIn was gently brought into contact with the SAM surface using a micromanipulator.

The SAM-bound bottom electrode was grounded and the EGaIn top electrode was biased.

Experimental Examples (1) FIG. 4 shows XPS spectra for the Ag$^{TS}$/SC$_{11}$PAH SAMs (PAH=BP, PYR, ANT, PHE, and NAP), FIG. 5 shows C$_1$s spectra for the SAMs, and FIG. 6 shows S2p spectra for the SAMs.

Table 1 shows the results of XPS analysis and contact angle measurements for the Ag$^{TS}$/SC$_{11}$PAH SAMs.

TABLE 1

| PAH | Atomic ratio (Exp.) | Atomic ratio (Calc.) | Contact Angle (°) |
| --- | --- | --- | --- |
| BP | 1.7 | 1.9 | 85 ± 1 |
| PYR | 1.6 | 1.5 | 93 ± 3 |
| ANT | 1.3 | 1.3 | 84 ± 2 |
| PHE | 1.3 | 1.3 | 85 ± 1 |
| NAP | 0.9 | 0.9 | 91 ± 3 |

The structures of the SAMs were analyzed by X-ray photoelectron spectroscopy (XPS). The XPS spectra exhibited the presence of carbon and sulfur elements in each SAM (FIG. 4). The ratio of sp$^3$ and sp$^2$ carbons was estimated from the deconvolution of the high-resolution spectra for Cis in FIG. 5. The experimental atomic ratio was determined by the ratio of the area under the sp$^3$ peak to the area under the sp$^2$ peak and the theoretical atomic ratio was calculated from the ratio of the number of sp$^2$ carbons to the number of sp$^3$ carbons in each compound. As can be seen from the results in Table 1, the C1s spectra of SC$_{11}$PAH (PYR) showed an atomic ratio of ~1.6, which was similar to the theoretical one (1.5). The S2p spectrum for the molecules (FIG. 6) showed spin-orbit doublets at ~163.0 eV and ~161.8 eV corresponding to S2p$_{1/2}$ and S2p$_{3/2}$, indicative of the presence of thiolate species, covalently linked to the Ag. Oxygen (O1s) is attributed to the presence of oxide- or surface-trapped water molecules.

(2) The characteristics of the SAMs were determined by the contact angle measurements (Table 1 and FIG. 7). As a result, all SAMs had contact angles (θ) of 87°±5°, which were significantly indistinguishable from each other.

(3) FIG. 8 shows histograms of log|J(V)| and log|r⁻| for the SAMs including the inventive compounds (PAH-terminated n-alkanethiols) and FIG. 9 shows heatmaps of the corresponding log|J|–V traces.

Table 2 shows the electrical properties of $Ag^{TS}$/$SC_{11}PAH$//$Ga_2O_3$/EGaIn junctions (8-15 junctions and 336-630 J-V traces).

TABLE 2

| PAH | Yield (%) | log|J(+1.0 V)|$_{mean}$ ± $\sigma_{log|J|}$ (log|J(+1.0 V)|$_{median}$) | log|J(−1.0 V)|$_{mean}$ ± $\sigma_{log|J|}$ (log|J(−1.0 V)|$_{median}$) | log|r⁻|$_{mean}$ ± $\sigma_{log|r^-|}$ (|r⁻|$_{mean}$ ± $\sigma_{|r^-|}$) |
|---|---|---|---|---|
| BP | 100 | −1.6 ± 0.3 (−1.7) | −0.2 ± 0.6 (−0.1) | 1.7 ± 0.3 (46.3 ± 1.9) |
| PYR | 100 | −2.6 ± 0.2 (−2.5) | −0.4 ± 0.2 (−0.5) | 2.2 ± 0.3 (148.0 ± 2.0) |
| ANT | 100 | −1.6 ± 0.4 (−1.7) | −1.9 ± 0.3 (−2.1) | −0.4 ± 0.2 (0.4 ± 1.6) |
| PHE | 88 | −2.0 ± 0.3 (−1.9) | −2.5 ± 0.6 (−2.3) | −0.3 ± 0.2 (0.5 ± 1.6) |
| NAP | 88 | −1.8 ± 0.5 (−1.7) | −1.6 ± 0.6 (−1.9) | −0.2 ± 0.2 (0.7 ± 1.6) |

As shown in FIGS. 8 and 9, the benzo[a]pyrenyl (BP)- and pyrenyl (PYR)-terminated n-alkanethiolates showed distinct asymmetric features in J, whereas the phenanthrenyl (PHE)-, anthracenyl (ANT)-, and naphthyl (NAP)-terminated n-alkanethiolates did not.

Mean, median, and standard deviation were extracted from the histograms and are shown in Table 2.

The mean value of r⁻ (|r⁻|$_{mean}$=~148) for $SC_{11}PYR$ was particularly indistinguishable from the median value (|r⁻|$_{median}$=~145), indicating statistically significant rectification. $SC_{11}BP$ also showed a rectification ratio of r⁻ (|r⁻|$_{mean}$=~46). In contrast, the other molecules showed no rectification (|r⁻|=~0.4-0.7). The standard deviations of r were in the range of 1.6-2.0.

(4) Since pure $Ga_2O_3$ in EGaIn an n-type semiconductor with a band gap of 4.8 eV, it can be assumed to play an important role in the rectification of $SC_{11}PYR$. Assuming that pyrene is a p-type organic moiety, the PYR//$Ga_2O_3$ top-interface might resemble a p-n junction, which explains the occurrence of rectification.

To test this hypothesis, the $Ga_2O_3$/EGaIn top electrode was replaced with a Au cantilever using conductive atomic force microscopy (CAFM) (FIG. 10). FIG. 11 is a histogram of J-V traces and r measured from the $Ag^{TS}$/$SC_{11}PYR$//$Au^{cantilever}$ junctions.

Large values of r⁻ (|r⁻|$_{mean}$=~79±2) similar to those of the EGaIn junction were recorded, indicating that rectification is not limited to the CAFM junction or the $Ga_2O_3$/EGaIn top electrode and stems from the $SC_{11}PYR$ molecule in the junction. The opposite polarity of rectification in the CAFM system to that in the EGaIn system resulted from the difference in electrical grounding; bottom and top electrodes were grounded for the EGaIn and CAFM junctions, respectively. These results are consistent with the results of previous studies that $Ga_2O_3$/EGaIn is likely to act as a metal rather than a semiconductor.

5) The atomic barrier created by the formation of the electrode-molecule-electrode junction is bias-dependent and determines the tunneling current flowing through the junction. The junction can be rectified in the structure of the invention as long as the termination of the insulating n-alkanethiolate with the conductive moiety creates an energy well at the barrier and the energy well can match the Fermi level ($E_F$) of the electrode at a bias of a polarity rather than at a bias of opposite polarities.

This was demonstrated experimentally through low temperature J-V measurements in previous studies using $SC_{11}Fc$. The energy coupling between the HOMO of Fc ($E_{HOMO}$=~5.0 eV, at 0 V) and the $E_F$ of $Ga_2O_3$/EGaIn (~4.3 eV at 0 V) at the SAM//$Ga_2O_3$ van der Waals interface increases |J (−1.0 V)|, not |J (+1.0 V)|. This leads to large rectification through thermally activated hopping by tunneling.

In the present invention, low temperature experiments were conducted in a low temperature probe station, temperature was lowered using liquid nitrogen under vacuum (~1×10⁻⁴ Torr), and J-V curves were recorded at variable temperatures (98-298 K). Surprisingly, the values of J(+V), J(−V) and r⁻ for PYR did not significantly change over the range of temperature (FIGS. 12-14).

This finding indicates that despite structural similarity between the PYR- and Fc-based junctions except the different terminal groups PYR and Fc, a hopping process is not involved in the rectification of $SC_{11}PYR$, as shown in FIGS. 12-14.

(6) Next, an experiment was conducted to more clearly demonstrate the rectifying properties of $SC_{11}PAH$ by varying the terminal PAH group to benzo[a]pyrenyl (BP), pyrenyl (PYR), anthracenyl (ANT), phenanthrenyl (PHE), and naphthyl (NAP), as shown in FIG. 3.

Interposed dipolar molecules can induce rectification. However, this hypothesis does not apply to the PAHs having no dipole moment. The change in the conjugation length of the PAHs varied the HOMO and LUMO energy levels, which were determined by UPS.

FIG. 16 shows plots of energy differences between the $E_F$ of $Ga_2O_3$/EGaIn and the $E_{MO}$ (energy of molecular orbital (HOMO or LUMO) of the PAHs. As shown in FIG. 16, the HOMO rather than the LUMO was overall close to the $E_F$ of the electrode and no rectification was observed before the value of $E_F$-$E_{MO}$ was lower than ~1.9 eV. This result suggests that the HOMO level relative to $E_F$ is important.

As discussed above, the large-area junction including the self-assembled monolayer (SAM) using each of the polycyclic-aromatic-hydrocarbon (PAH)-terminated compounds showed excellent rectifying properties by charge-tunneling. In particular, the pyrenyl-terminated n-alkanethiolate greatly rectified the tunneling current. Specifically, the r⁻ was ~148 for the terminal pyrenyl group having a long conjugation length and ~46 for the terminal benzo[a]pyrenyl group. No rectification was observed in the PAHs having relatively short conjugation lengths, such as phenyl, anthracenyl, and phenanthrenyl groups.

Therefore, the polycyclic-aromatic-hydrocarbon (PAH)-terminated compounds are suitable for use in molecular rectifiers. In addition, the use of the PAH-terminated compounds can overcome the limitation of performance improvement by current integration technology of semiconductor devices.

In addition, it was demonstrated that rectification relies on pure tunneling rather than on thermally activated hopping. A further experiment for CAFM revealed that rectification is not derived from or limited by the EGaIn top electrode. UPS analysis of the SAMs revealed that rectification occurs when HOMO, an accessible molecular orbital of the PAH, approaches the Fermi level of the top electrode.

(7) To understand the rectification of the SC$_{11}$PAH junctions in more detail, the inventors of the present invention considered a Landauer expression (Equation 1) for which $$I = \frac{2e}{h} \int_{-eV/2}^{eV/2} T(E, \varepsilon, \Gamma) dE$$

The inventors of the present invention assume off-resonant tunneling, zero temperature, and no significant differences in interaction inside the monolayer across different PAH groups. In Equation 1, e is the fundamental unit of charge, h is Planck's constant, and V is the applied voltage. By considering a transport via single electron level, the transmission function T (E, ε, Γ) is assumed to be a single Lorentzian, as shown in Equation 2:

$$T(E) = \frac{\Gamma^2/4}{(E - \varepsilon - \alpha eV)^2 + \Gamma^2/4}$$

It depends on the energy (E), the molecular energy level (ε), and the molecule-electrode coupling strength (Γ). In the transmission function, α is the dimensionless constant controlling the shift of the molecular level with respect to the electrode chemical potential under an external bias and approximates the first-order variation (linear Stark shift) upon application of a bias. For α=0, the molecular energy level does not shift relative to the electrode chemical potential by the applied bias, and there is no rectification (a of FIG. 17). In the case of α<0, the molecular energy level tends to be pinned to the EGaIn top-electrode chemical potential and yields rectification (b of FIG. 17). When the Ga$_2$O$_3$/EGaIn tip is biased negatively relative to the Ag$^{TS}$ substrate, the molecular energy level (HOMO) of PAH moves up; consequently, a larger fraction of the HOMO resonance peak enters the bias window, whereas, at positive tip bias, the portion of HOMO peak inside the bias window is significantly decreased, resulting in a low current.

All measured molecules possess the alkyl backbone (n-undecanethiolate) with large HOMO and LUMO gaps (~8 eV) and the n-alkyl chain electronically isolates the PAH from the $E_F$ of the bottom electrode, and the molecular resonance energy is taken in the transmission function from the frontier orbital of PAH. Indeed, DFT calculation of SC$_{11}$PYR molecule showed that HOMO and LUMO are positioned on the PYR group. With Equations 1 and 2, the inventors of the present invention simulated I-V traces and fitted experimental data. The inventors of the present invention focused on fitting of rectification behavior rather than the absolute values of currents. From fitting values of α, ε, and Γ were extracted. The inventors of the present invention initially took the transmission function modeled with a single Lorentzian peaked at orbital energy of PAH, the closest to the $E_F$ of the top electrode. Ultraviolet photoelectron spectroscopy (UPS) analysis combined with optical band gap analysis showed that the HOMO was in proximity to the $E_F$ of Ga$_2$O$_3$/EGaIn for the PYR and BP molecules, whereas the LUMO was in proximity to the $E_F$ of Ga$_2$O$_3$/EGaIn for the NAP, PHE, and ANT molecules.

b of FIG. 17 shows an exemplary fitting result for PYR. The experimentally measured asymmetric feature in I-V curves was roughly fit to the simulated one except for current behavior at a high bias regime at +V. The increase in current in the high bias regime at +V resulted in the regression of |r$^-$| in the high bias regime, as shown in c of FIG. 17. However, the single Lorentzian model failed to account for this, which concluded that not only HOMO but also LUMO should be involved in charge tunneling. Thus the inventors of the present invention repeated the simulation and fitting using a transmission equation corrected with the double Lorentzian model. As a result, the better fitting for all molecules could be achieved, as summarized in Table 3.

TABLE 3

| PAH | α | $E_{F-\varepsilon HOMO}$ (eV)[a] | $E_{F-\varepsilon LUMO}$ (eV)[b] | $E_{F-\varepsilon HOMO}$ (eV)[c] | $E_{F-\varepsilon LUMO}$ (eV)[c] | $\Gamma_R$ (eV)[c] | $\Gamma_L$ (eV)[d] |
|---|---|---|---|---|---|---|---|
| BP  | −0.4  | 1.2 | 1.9 | 0.65 | 1.25 | 0.035 | 0.003 |
| PYR | −0.4  | 1.4 | 2.1 | 0.7  | 1.35 | 0.050 | 0.003 |
| ANT | −0.08 | 1.9 | 1.3 | 1.0  | 0.9  | 0.020 | 0.003 |
| PHE | −0.06 | 2.4 | 1.7 | 1.3  | 1.2  | 0.025 | 0.003 |
| NAP | −0.03 | 2.1 | 2.1 | 1.3  | 1.25 | 0.025 | 0.003 |

[a]Measured by ultraviolet photoelectron spectroscopy (UPS).
[b]Estimated by adding the optical gap to the HOMO energy measured by UPS.
[c]Obtained from fitting of experimentally measured I-V traces with the Landauer formula (Equation 1) and double Lorentzian model-based transmission function.
[d]All molecules have the same S-Ag interface, and thus the same value of $\Gamma_L$ was used.

The rectification of SC$_{11}$PAH relied on the Stark shift parameter (α), as hypothesized above. Further simulation study also indicates that varying Γ values while keeping α=0 did not cause significant rectification. These results led to the conclusion that the high rectification ratios for PYR and BP are attributed to the shift of molecular resonance energy. The molecular resonance energies extracted from junction measurements were largely perturbed compared with those of the identical SAMs characterized by UPS, leading to a significant reduction of the HOMO-LUMO gap (d of FIG. 17). This gap reduction in charge transport could be explained by the image charge effect frequently observed in molecular tunnel junctions. First of all, the transmission functions for the real molecular junctions do not have the form of the perfect Lorentzian, as assumed in the modeling. In addition, the dependence of molecular resonance energy on the applied bias might not be purely linear for the Stark shift. In addition, the applied bias can have an impact on the molecular orbital shape, resulting in the change of the coupling strengths of the molecular levels to the electrodes.

Two separate control experiments were further conducted to confirm the validity of the simulations. First, to test if the polarity of α values in the simulations above was relevant to rationalizing the experimental data, I-V simulations were repeated with the α values of the same magnitude and opposite polarity. As a result, it was found that the change of polarity of α values reversed the direction of rectification and did not fit the experimental results. Next, to test if the double Lorentzian model based on HOMO and HOMO-1 of PAH, rather than the HOMO and LUMO, could fit the experimental data, I-V simulations were repeated with the HOMO and HOMO-1 estimated from the DFT calculation. The simulation results indicate that the inclusion of HOMO and HOMO-1 into the transmission function did not yield significant rectification and poorly fit the experimental data.

The Stark shift is equivalent to the change of energy offset of ε with respect to $E_F$ upon the application of a bias, as described in the transmission function. From a tunneling barrier point of view, the relative comparison of the barrier's height in the absence and presence of an external electric field should be translated into the degree of asymmetry in the junction (here defined quantitatively as a). Therefore, the Stark shift of molecular energy resonance was further evaluated by analyzing the measured j-v traces with transition voltage spectroscopy (TVS). When the transmission function can be well described by a Lorentzian form, TVS is a useful spectroscopic tool in molecular electronics and allows one to probe effective molecular resonance energy during operation through the measurement of transition voltage ($V_t$), the minimum voltage obtained from Fowler-Nordheim plot. The $V_t$ is proportional to $|\varepsilon-E_F|$ provided that $|\varepsilon-E_F| \gg V_t$, where the proportionality constant is related to the asymmetry factor, u. Therefore, the relative ratio of $|\varepsilon-E_F|/e$ to $V_t$ could be an indication of symmetry/asymmetry of junction; a symmetric junction exhibits $|\varepsilon-E_F|/e \approx V_t$. The plot of $|\varepsilon-E_F|/V_t$ values estimated from experimental (UPS) and fitting data as a function of a values in a of FIG. 18 shows that the increased ratio (a factor of ~4.2 and ~2.5 for experimental and fitting data, respectively) of $|\varepsilon-E_F|/V_t$ from nonrectifying to rectifying PAHs is correlated with that (a factor of ~5.0) of a. This indicates that the molecular energy level for the molecule with a large a is shifted to the substrate ($Ag^{TS}$) chemical potential by the finite bias voltage, resulting in the small $V_t$ and large $|\varepsilon-E_F|/V_t$ values. Although little has been unveiled about what types of chemical features in organic molecules are associated with the Stark shift, another work involving the Stark effect in different nanomaterials (e.g., quantum dots) allowed to take into account the polarizability of materials. The quantum-confined Stark effect in a single CdSe quantum dot (with ~4 nm radius) has been characterized by the highly polarizable excited state resulting from photoexcitation. Considering this stimulating work, intuitively, more polarizable PAH would undergo more charge redistribution upon the application of a bias, stronger electrostatic interaction with the electrode being in contact, and hence a larger Stark shift. Indeed, the plot of |α| against polarizability for the model structure of PAHs (b of FIG. 18) showed that there is an approximate correlation between the two values, suggesting the role of polarizability in the Stark shift-induced rectification.

There was a slight decrease by a factor of 3 in the rectification ratio when the conjugation length was further increased from PYR to BP. This is probably due to changes in the degree of asymmetric charge distribution of the orbital energy in biases of opposite polarities or the distance between the PAH terminal group and the EGaIn top electrode. In addition, the significant rectification occurred when a phenyl ring was added to the ANT to form the PYR. This could be rationalized with the change of electronic structure resulting from the structural modification. The UPS data indicated that the energy offset of HOMO with respect to the $E_F$ of EGaIn was reduced by ~36% upon the structural change from ANT ($|\varepsilon_{HOMO}-E_F|=\sim1.9$) to PYR (~1.4).

The reduced energy offset yielded the more accessible molecular orbital energy state and hence the remarkable rectification. Another rectifying PAH, the BP molecule, also showed a decreased energy offset value (~1.2) as compared with the nonrectifying ANT molecule, whereas the other nonrectifying PAHs, the PHE and NAP molecules, showed relatively large energy offset values of ~2.4 and ~2.1, respectively.

Recently, another research group has also suggested that the Stark effect is a possible origin for achieving a large rectification ratio. This work theoretically showed that the Stark effect can induce a significant rectification ratio up to ~500 in n-alkanethiolates at ±1.5 V. However, experiments showed the modest rectification ratio of ~1.5 once CAFM was used to measure tunneling currents for n-alkanethiolates of different lengths ($SC_n$, where n=7, 8, 9, 10, 12). Such a marked difference in experimental and calculation results was attributed to nonideal molecule-electrode contact in reality that screened the Stark effect. Herein, it was demonstrated that the Stark-effect-induced significant rectification up to ~170 at ±740 mV could be achieved by a chemical means that controls the structure of PAHs terminated in n-alkanethiolates.

In summary, the present invention demonstrated a chemical means with which to control the Stark shift of molecular energy resonance and create hydrocarbon-based molecular diodes with significant rectification ratios. The present invention has also shown that rectification is attributed to the Stark effect in large-area molecular tunnel junctions. In addition, the Stark effect was discovered by taking advantage of the fine-tunability of structurally simple PAHs to modulate conjugation length. Given that singling out factor(s) associated with Stark effect in many cases of molecular-scale devices is difficult to achieve, the results reported herein are believed to delineate the mechanism of the Stark effect in the molecular junction. Based on these results, it is envisaged that various molecular devices and systems can be designed and fabricated beyond PAHs through control of the Stark effect.

INDUSTRIAL APPLICABILITY

The compound of the present invention can exhibit rectifying properties when introduced between electrodes. Therefore, the compound of the present invention can be utilized as an organic material in a molecular rectifying electronic device. Particularly, the use of the compound enables the fabrication of vertically or horizontally structured molecular rectifying electronic devices or devices consisting of an array of such molecular electronic devices.

The molecular rectifier of the present invention can achieve a high rectification ratio when driven at low voltage. Therefore, the molecular rectifier of the present invention can replace a silicon-based diode device. Particularly, the molecular rectifier of the present invention is industrially applicable to wearable devices, Bluetooth devices, and IoT devices where low voltage driving is required.

In addition, the end of the compound according to the present invention is anchored to an electrode to effectively form a self-assembled molecular layer on the surface of the electrode. Due to this advantage, a molecular electronic device can be easily fabricated by placing a top electrode on the self-assembled molecular layer.

Furthermore, the basic rectifying properties of the material for the self-assembled molecular layer can be directly measured by conductive atomic force microscopy (CAFM) on the surface of the self-assembled molecular layer to clearly establish the principle of rectification.

The invention claimed is:

1. A compound for a molecular electronic device, represented by Formula I:

$$R_1-(CH_2)_n-SR_2 \quad \text{[Formula I]}$$

wherein $R_1$ is a $C_{10}$-$C_{40}$ polycyclic aromatic hydrocarbon group, $R_2$ is a $C_1$-$C_7$ alkyl or acetyl group, and n is an integer from 1 to 20.

2. The compound according to claim 1, wherein $R_1$ is selected from pyrenyl and benzopyrenyl groups.

3. The compound according to claim 1, wherein the compound is a molecular rectifying compound.

4. A molecular electronic device comprising a first electrode, a second electrode opposite to the first electrode, and a molecular layer bound to the surface of the second electrode wherein the molecular layer is formed by self-assembly of the compound represented by Formula I:

$$R_1-(CH_2)_n-SR_2 \quad \text{[Formula I]}$$

wherein $R_1$ is a $C_{10}$-$C_{40}$ polycyclic aromatic hydrocarbon group, $R_2$ binding to the surface of the second electrode is a $C_1$-$C_7$ alkyl or acetyl group, and n is an integer from 1 to 20.

5. The molecular electronic device according to claim 4, wherein $R_1$ is selected from pyrenyl and benzopyrenyl groups.

6. The molecular electronic device according to claim 4, wherein the molecular electronic device is a molecular rectifying device.

* * * * *